US011294077B2

(12) United States Patent
Petrak

(10) Patent No.: US 11,294,077 B2
(45) Date of Patent: Apr. 5, 2022

(54) METHOD AND DEVICE FOR MULTI-DIMENSIONAL DIRECTION MEASUREMENT OF GAMMA RADIATION IN THE FAR FIELD

(71) Applicant: Hellma Materials GmbH, Jena (DE)

(72) Inventor: Sibylle Petrak, Jena (DE)

(73) Assignee: Hellma Materials GmbH, Jena (DE)

( * ) Notice: Subject to any disclaimer, the term of this patent is extended or adjusted under 35 U.S.C. 154(b) by 4 days.

(21) Appl. No.: 17/101,537

(22) Filed: Nov. 23, 2020

(65) Prior Publication Data
US 2021/0173096 A1 Jun. 10, 2021

(30) Foreign Application Priority Data

Nov. 22, 2019 (DE) .................... 10 2019 131 695.2
Nov. 22, 2019 (DE) .................... 10 2019 131 696.0

(51) Int. Cl.
*G01T 1/167* (2006.01)
*G01T 1/164* (2006.01)
(Continued)

(52) U.S. Cl.
CPC .............. *G01T 1/167* (2013.01); *A61B 6/037* (2013.01); *G01T 1/1642* (2013.01);
(Continued)

(58) Field of Classification Search
CPC ....... A61B 6/037; G01T 1/167; G01T 1/1642; G01T 1/1644; G01T 1/2985; G01T 7/00;
(Continued)

(56) References Cited

U.S. PATENT DOCUMENTS

2002/0011571 A1 1/2002 Lin et al.
2004/0251418 A1 12/2004 Gunter
2009/0256080 A1 10/2009 DeVito

OTHER PUBLICATIONS

A. Gueorguiev, J. Preston, L. Hoy, G. Pausch, C. -M. Herbach and J. Stein, "A novel method to determine the directionality of radiation sources with two detectors based on coincidence measurements," IEEE Nuclear Science Symposuim & Medical Imaging Conference, 2010, pp. 1525-1530 (Year: 2010).*

* cited by examiner

*Primary Examiner* — David P Porta
*Assistant Examiner* — Gisselle M Gutierrez
(74) *Attorney, Agent, or Firm* — Buchanan Ingersoll & Rooney PC

(57) ABSTRACT

A method for multidimensional direction measurement of gamma radiation in the far field by means of a group of several energy discriminating detectors synchronized with each other for detection of radiation can use unidirectional and bidirectional Compton scattering processes and lookup tables $LUT^{SK}$, a defined functional value $f(E1,E2)$, a list of defined detector pairs with an identification number i for defined detector pairs, and one or more frequency distributions $Y$ for the acquisition of the measurement values. In some embodiments, the method can include setting up a detector system, acquiring measurement values, associating coincidence events with an Identification number, calculating a functional value, acquiring coincidence events in frequency distributions, and calculating one or more direction distributions from the frequency distributions.

15 Claims, 17 Drawing Sheets

(51) Int. Cl.
*A61B 6/03* (2006.01)
*G01T 1/29* (2006.01)
*G06T 11/00* (2006.01)
*G01T 7/00* (2006.01)

(52) U.S. Cl.
CPC .......... *G01T 1/1644* (2013.01); *G01T 1/2985* (2013.01); *G06T 11/006* (2013.01); *G01T 7/00* (2013.01); *G06T 2211/421* (2013.01)

(58) Field of Classification Search
CPC ................ G01T 1/2907; G06T 11/006; G06T 2211/421
USPC ........................................................ 250/393
See application file for complete search history.

(a) 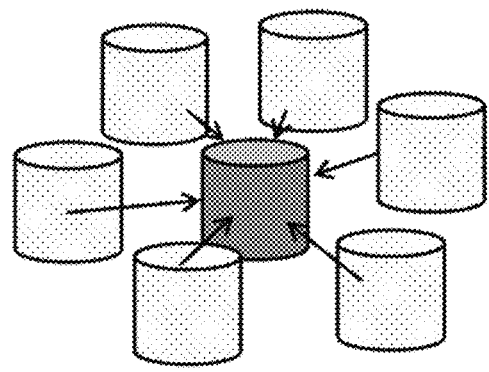 (b) 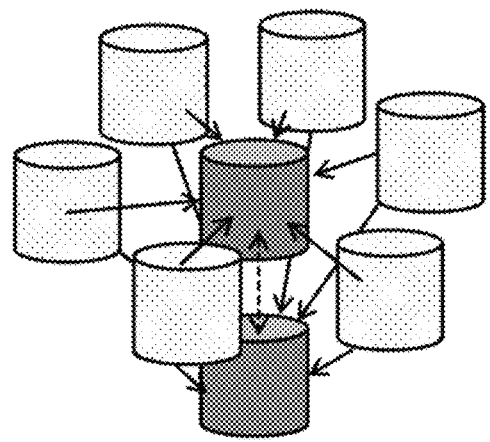
Fig. 4a                                Fig. 4b (a) 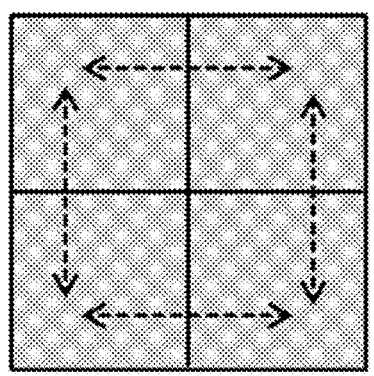  (b) 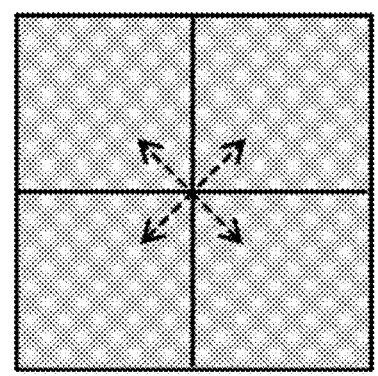
Fig. 6a  Fig. 6b

Frequency distribution Y for the 3-dimensional direciton measurement
| SK = 1 | SK = 2 | SK = 3 |
|---|---|---|
| Detector Pairs I to VI | Detector Pairs VI to XII | Detector Pair XIII |
| 1 = plastic, 2 = CeBr₃ top | 1 = plastic, 2 = CeBr₃ bottom | 1 = CeBr₃ top, 2 CeBr₃ bottom |
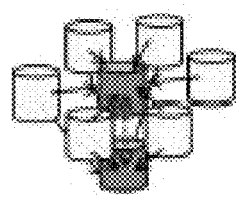
$$A = \frac{E2-E1}{E1+E2}$$
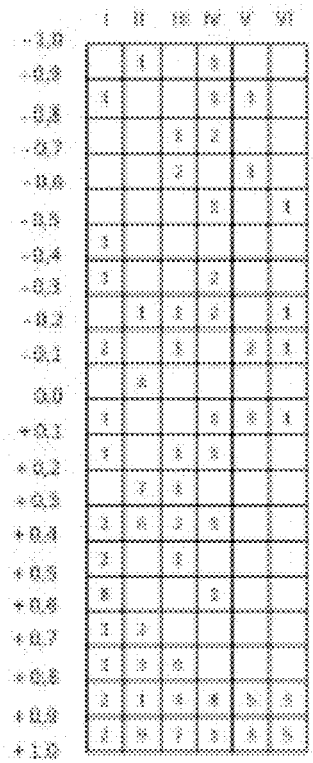
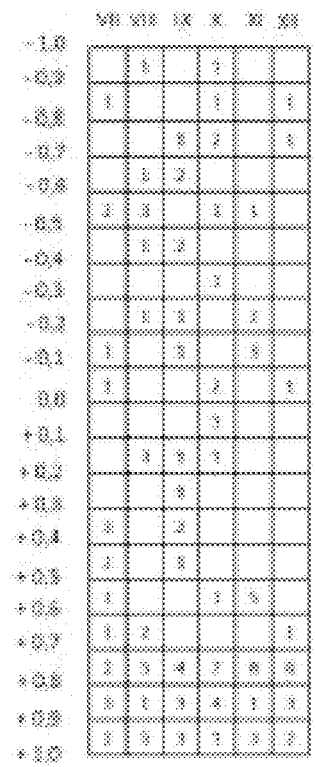
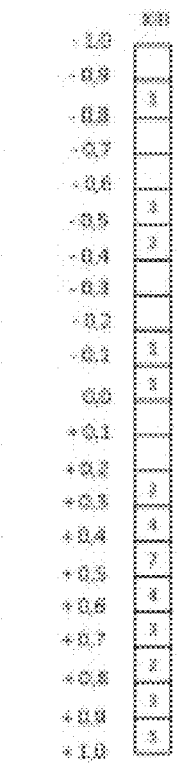
Fig. 7

Direction Distribution (a) for 2 dimensional measurement (b) for 3 dimensional measurement LUT
for symmetry class
from CEBr$_3$ – plastic detector pairs
nuclide: Co-60

Angle $\vartheta$ ⟶

$$A = \frac{E2 - E1}{E1 + E2}$$

| | 0° | 5° | 10° | 15° | | | | | | | | 180° |
|---|---|---|---|---|---|---|---|---|---|---|---|---|
| -1.0 | 21 | 33 | 32 | 30 | | | | | | | | 11 |
| -0.9 | 85 | 60 | 70 | 101 | | | | | | | | 85 |
| -0.8 | 137 | 114 | 127 | 126 | | | | | | | | 63 |
| -0.7 | 67 | 79 | 84 | 84 | | | | | | | | 113 |
| -0.6 | 48 | 51 | 41 | 54 | | | | | | | | 48 |
| -0.5 | 45 | 46 | 36 | 36 | | | | | | | | 39 |
| -0.4 | 24 | 39 | 38 | 52 | | | | | | | | 22 |
| -0.3 | 28 | 34 | 34 | 45 | | | | | | | | 17 |
| -0.2 | 27 | 30 | 36 | 31 | | | | | | | | 16 |
| -0.1 | 29 | 33 | 35 | 41 | | | | | | | | 5 |
| 0.0 | 33 | 49 | 42 | 62 | | | | | | | | 2 |
| +0.1 | 31 | 46 | 39 | 61 | | | | | | | | 38 |
| +0.2 | 47 | 58 | 80 | 68 | | | | | | | | 39 |
| +0.3 | 75 | 85 | 113 | 145 | | | | | | | | 13 |
| +0.4 | 108 | 98 | 154 | 173 | | | | | | | | 13 |
| +0.5 | 183 | 204 | 196 | 219 | | | | | | | | 11 |
| +0.6 | 255 | 265 | 271 | 283 | | | | | | | | 19 |
| +0.7 | 322 | 324 | 293 | 296 | | | | | | | | 25 |
| +0.8 | 314 | 298 | 221 | 197 | | | | | | | | 30 |
| +0.9 | 283 | 131 | 176 | 104 | | | | | | | | 15 |

Fig. 9

Measurement plan with angular positions of a reference source for creating the LUT

METHOD AND DEVICE FOR MULTI-DIMENSIONAL DIRECTION MEASUREMENT OF GAMMA RADIATION IN THE FAR FIELD

CROSS-REFERENCE TO RELATED APPLICATIONS

The present application claims priority to German Patent Application Nos. 10 2019 131 696.0 and 10 2019 131 695.2. The entirety of these German patent applications are incorporated by reference herein.

FIELD

The invention relates to a method as well as to a device for radiation detection, in particular, a detector system measuring the direction for measurement of the direction distribution of the radiation intensity. The method supports the 3-dimensional as well as the 2-dimensional direction measurement of one or more radiation sources in the far field.

BACKGROUND

In ABC and radiation protection, there exists a demand for handy, compact radiation measurement devices, which are able to provide direction information. In contrast to imaging in medicine, where activity concentrations are illustrated, here, the direction measurement means determining the directions of one or more radiation sources in order to support the detection of radiation sources. Compact gamma spectrometers and nuclide identification devices belong to prior art. Such devices, however, are not able to determine the angle of incidence of the radiation.

At present, a detection of radiation sources in the field is only possible, if emergency forces walk or drive through the entire area with a radiation measurement device in order to acquire an intensity distribution. The method is very complex and is not always applicable, if e.g., radiation sources are to be located in an inaccessible area.

Complex devices composed of many single detectors, which are employed for medical imaging, are known from the clinical field. These devices are complex and require complex algorithms for the data analysis, which requires substantial computing capacity. The algorithms calculate the activity concentrations of a radiopharmaceutical in a patient in immediate vicinity to the radiation detectors (near field). Basically, these algorithms may also be used for the compact devices with directional resolution mentioned above as far as they are adapted to the operating conditions for ABC and radiation protection.

For this, the methods have to be rearranged from the near field to the far field. The computing effort has to be reduced that much that data processing in real-time is possible in parallel to the data acquisition such that the results are available live during the measurement. Further, there are differences with respect to the radiation intensity. During the detection of radioactive radiation sources, the radiation intensities registered at the detection location frequently lie below the ones that are common in medicine. This poses increased requirements to the algorithms, which have to be yield reliable and reproducible resides despite statistical limitations of the data sets. The direction measurement, also, has to function reliably, if the radiation intensity of the sources to be measured lies below the level of the natural background radiation. Therefore, it is necessary that the natural background radiation is considered in the analysis.

For the localization of radiation sources in the field, also, fast methods are required, which reconstruct a radiation far field, which are also usable with low counter statistics, and which take the effect of natural radiation into consideration.

Several methods are known, which have been developed for the localization of radiation sources in the field. US2012/0043467 describes a method for Single Plane Compton cameras, which is suitable for the direction measurement of a radiation source. However, this method has the disadvantage that it is restricted to the direction measurement of one radiation source per radio nuclide, and is not able to measure a direction distribution of several radiation sources. Further, U.S. Pat. No. 8,461,547 B2 describes a method, which uses the direction information of Compton scattering processes in order to determine the direction of a radiation source. The methods according to prior art, thereby, do not use image reconstruction methods; rather, simple statistical analysis techniques are employed.

SUMMARY

Therefore, it is an object to provide a method for compact, direction-resolving radiation measurement devices, which also can be used for combined systems made up of several radiation detectors, and for segmented radiation detectors.

Therefore, embodiments of the invention can be based on the object to overcome the disadvantages of the methods known from prior art. In particular, a reliable and efficient detection of several radiation sources should be provided without a restriction to the number of radiation sources.

Embodiments of the inventive method for multidimensional direction measurement of gamma radiation in the far field by means of a group of several energy discriminating detectors that are synchronized with each other for the detection of radiation is characterized in that the method uses unidirectional and bidirectional Compton scattering processes and lookup tables $LUT^{SK}$, a defined functional value $f(E1, E2)$, a list of defined detector pairs with an identification number i for defined detector pairs, and one or more frequency distributions $\underline{Y}$ for the acquisition of measurement values. The method according to the invention comprises the following steps:

a) setting up the detector system for a measurement, comprising the following steps:

creating a list with defined detector pairs, wherein the defined detector pairs comprise all pairs, which may be formed in combination from the quantity of detectors, and wherein each pair comprises at least one detector from a material having an atomic number of $Z_{eff}>30$, and indicating these with an ID-number i;

interconnecting all detectors in a coincidence circuit such that the coincidence events are acquired in all defined detector pairs $i=1, \ldots, I$;

identifying both detectors of each defined detector pair i with the numbers 1 and 2, respectively, wherein the detector having the lower atomic number receives the number 1 and that one having the higher atomic number, the number 2, wherein if both detectors consist of the same material, the identification of 1 and 2, respectively, is made arbitrarily;

defining a function $f(E1, E2)$ which is calculated from two energy values E1 and E2, wherein such functions $f(E1, E2)$ are allowable, which are traceable back to a function $f(E1)$ when substituting E2 by C–E1, which function over the entire interval $[0,C]$ is clearly defined, constant, and monotonous, wherein C is a constant, which represents the radiation energy C=E1+E2;

b) acquiring measurement values of coincidence events, if interactions take place simultaneously in two detectors of all defined detector pairs i, wherein the measurement values originate from a radiation distribution in the far field, and the measurement values are interaction energies E1 and E2 of the radiation measured in the detectors;

c) associating coincidence events with a n identification number i;

d) calculating the functional value f(E1, E2) from two energy values E1, E2 per coincidence event by means of the function f(E1, E2) defined in step a);

e) acquiring the coincidence events corresponding to their identification number i and their functional values f(E1, E2) in one or more frequency distributions $\underline{Y}$, wherein a separate frequency distribution $\underline{Y}$ is available for each radio nuclide, f) calculating one or more direction distributions $\underline{X}$ from the frequency distributions $\underline{Y}$ by means of a statistical image reconstruction method of emission tomography using lookup tables $LUT^{SK}$, wherein a separate direction distribution $\underline{X}$ is available for each radio nuclide.

Embodiments of the method for direction measurement of a radiation distribution in the far field according to the invention can be applicable for combined systems made up from several radiation detectors as well as for segmented radiation detectors. In one case, a group of several radiation detectors is interconnected to each other, and in another case, the active detector medium is subdivided into several units. The group of radiation detectors and the segmented single detector, respectively, form a temporally synchronized system. Each detector and each segment, respectively, is able to measure the energy of the radiation, which is deposited there by interaction, and may be synchronized with other detectors and segments, respectively. A detector within the meaning of the invention is considered as a radiation detector or a detector segment, respectively, which is able to detect radiation and which can be read out individually.

It is assumed that the measurement system is equipped with data acquisition in the list mode, and is able to process the data of each detector and each segment, respectively.

Embodiments of the method according to the invention can be specifically suitable for stationary or almost stationary direction measurement, wherein basically two embodiments are specifically advantageous, namely, the three-dimensional direction measurement and the two-dimensional direction measurement.

The two-dimensional direction measurement is a specific case of the direction measurement, when all of radiation sources are lying in one plane, for example, in the horizontal plane. Groups of planar radiation detectors represent suitable device types for the two-dimensional direction measurement. Thereby, the apparatus is oriented such that the detection plane is identical to the plane of the radiation sources.

Embodiments of the method for direction measurement according to the invention can be referred to as direction resolving coincidence spectroscopy. In coincidence spectroscopy, coincidences are examined, according to which interactions take place in respectively two detectors (or segments) of the measurement devices simultaneously. Pairs of respectively two detectors are the basic imaging elements of the direction measurement. The energy inputs E1 and E2 registered in a coincidence detector pair are considered together with the spatial orientation of the detector pair.

The direction resolved coincidence spectroscopy can use uses two interaction processes of gamma radiation: the Compton scattering and the photoelectric absorption.

The measurement device is considered as a combination of detector pairs. At first, some definitions for the detector pairs will be specified.

Those detector pairs are selected, which are to be used for the direction measurement. For the selection, it is helpful, to consider the materials at first, from which the detectors are made up. It is sufficient to subdivide the materials into two classes. One group is formed by materials of medium to high atomic number. Within the meaning of the invention, a medium to high atomic number is considered as a number $Z_{eff}$ higher than 30. If the detector materials are present as chemical compound, then $Z_{eff}$ is considered as the effective atomic number that means the mean atomic number of all elements comprised in the compound considering the atomic masses of the elements and their stoichiometric composition.

For example, detector materials of medium to high atomic number $Z_{eff}>30$ are NaI, a frequently used material in scintillation detectors, and also halides of rare earth, as $CeBr_3$, $LaBr_3$, $LaCl_3$ and $La(Br_xCl_{1-x})_3$. In particular, Ge, GaAs, CdTe and CdZnTe are to be mentioned as semiconductor materials having a medium to high atomic number. These materials are characterized by their high probability for photoelectric absorption in the energy range of some 10 keV to 3 MeV.

The other group comprises detectors from materials of low atomic number, the atomic number $Z_{eff}$ of which is smaller than 30. Plastic scintillators belong to this group, organic crystals as antrahcene, stilbene or p-terphenyl, pure or doped crystals, as for example, $CaF_2$:Eu and the semiconductor material is silicon. The materials having a low atomic number of $Z_{eff} \leq 30$ have a high probability for Compton scattering in the energy range from 100 keV to 3 MeV.

Two types of detector pairs may be formed from these two groups of detectors, by means of which the incident radiation may be determined. It is distinguished between unidirectional and bidirectional detector pairs. Both types of detector pairs are different with respect to the direction of the scattered radiation.

A unidirectional detector pair comprises a detector from the group having a low atomic number as well as a detector from the group having a medium to high atomic number. If, for example, a plastic detector and a cerbromide detector are combined with each other, this is a unidirectional detector pair. In a unidirectional detector pair, each detector has a unique physical function. If a coincidence event is observed with the radiation energy E1+E2 belonging to the nuclide, it is possible, to determine unambiguously that the incident radiation has been scattered in the plastic detector at first, prior to being absorbed in the cerbromide detector. The reverse situation that the radiation has been scattered in the cerbromide detector at first prior to being absorbed in the plastics detector has a probability close to zero.

The direction of the scattered radiation is known in a unidirectional detector pair. The radiation is scattered in the detector having a low atomic number towards the detector having a high atomic number.

Bidirectional detector pairs consist of a combination of respectively two detectors from the group of medium and high atomic number, also, for example, of cerbromide with cerbromide or germanium with germanium. When using segmented semiconductor detectors, pairs from respectively two segments also are bidirectional, because both segments consist of the same material.

In a bidirectional pair—as far as no other information is available—it cannot be determined, which one of the two detectors has scattered the incident radiation at first. The direction of the scattered radiation remains unknown. The radiation may have been scattered from detector 1 to detector 2, but also from detector 2 two detector 1.

It is to be noted that unidirectional as well as bidirectional detector pairs are limited in their direction determination with respect to the incident radiation. The direction of the incident radiation cannot be reconstructed unambiguously with a single coincidence event. For the two-dimensional case, the incidence direction is set to a V-line, for the three-dimensional case, it is set to a surface of the cone. The measurement data of a single event do not allow for any statements with respect to which arm of the V-line or in which direction of the surface of the cone the radiation source is lying.

With respect to the direction reconstruction of the incident radiation, the unidirectional and bidirectional detector pairs provide equal information. The measurement data of many coincidence events, in both cases, have the statistical properties required for the direction measurement. The fact that the direction of the scattered radiation is not known in a bidirectional detector pair does not represent an experimental restriction with respect to the direction determination of the incident radiation.

As outlined in the following in further detail, the technique of the direction resolving coincidence spectroscopy has as an essential characteristic feature the that it may be used for unidirectional as well as for bidirectional detector pairs.

The detectors of a device may be shared multiply by different pairs. The number of combination possibilities is determined by the detector materials. Detectors from the group of low atomic number may be combined with any detector from the other group having a medium or high atomic number. Detectors from the group having a medium or high atomic number may even be combined with any other detector in the device to a pair.

The group of detectors having a low atomic number is, on the other hand, not suitable for a combination of pairs within a group.

A measurement procedure may use a combination of unidirectional and bidirectional detector pairs, or may exclusively use unidirectional or exclusively bidirectional pairs for the direction measurement.

After the unidirectional and bidirectional detector pairs have been selected and have been provided with an identification number i, both detectors of the pairs are indicated by the numbers 1 and 2, respectively. If a pair comprises different detector materials, then the detectors of the materials having the lower atomic number are indicated as 1, and the detectors of a material having the higher atomic number as 2. If the pairs consist of detectors made up from the same material, the decision, which detector from the pair is indicated as 1 and 2, respectively, may be taken arbitrarily, as far as this is maintained consistently throughout the data analysis.

In the following, it is assumed that all radiation detectors are calibrated for energy measurement. In the measurement process, coincidence events are required, which form a triple according to their energy values E1 and E2 in the detectors 1 and 2 and the spatial limitation of the detector pairs. The spatial orientation is represented by the identification number i of the detector pair. The two energy values E1 and E2 comprise information which, on the one hand, identifies the nuclide, the radiation of which is observed, but on the other hand, also measures the direction, from which the radiation arrives at the detector pair. Due to energy conservation, the sum of the registered energy inputs E1+E2 is set to the radiation energy of the nuclide. Both measurement values E1 and E2 are strongly correlated with each other, and the direction information is substantially comprised in the difference E2−E1. Therefore, it is possible to reduce the number of the variables by defining a new measurement value f(E1, E2) from both energy values E1 and E2, which approximately represents the direction information. The measurement data (i, E1, E2) that at first have been organized as a triple may thus be reduced to a duple with the two features i and f(E1, E2).

Because stationary or almost stationary measurement conditions or assumed, the measurement data may be grouped as two-dimensional frequency distribution $\underline{Y}$. Each event is sorted according to its two features i and f(E1, E2) in the frequency distribution $\underline{Y}$.

For the acquisition of the measurement data, a histogram is created for each detector pair i. For these histograms, the value range of f(E1, E2) is to be subdivided into classes. If a coincidence event is registered, then a suitable functional value f(E1, E2) may be calculated from the two energy values E1 and E2 in the detectors 1 and 2, respectively. Such functions f(E1, E2) are allowable within the meaning of the invention, which are traceable back to a function f(E1) when substituting E2 by C−E1, which function over the entire interval [0, C] is clearly defined, constant, and monotonous. The value C is a constant, which represents the radiation energy C=E1+E2.

According to a further preferred embodiment of the method according to the invention, the functional value f(E1, E2) used in the steps a) and d) is the energy asymmetry (E1, E2)=(E2−E1)/(E1+E2).

An allowable function, for example, is the energy asymmetry A $$f(E1, E2) = A = \frac{E2 - E1}{E1 + E2} \tag{23}$$

When substituting E2 by C−E1 in eq. (1) the function f(E1)=1−2E1/C is created, which is clearly defined, constant, and monotonous over the entire interval [0,C]. Functions having the above mentioned properties are suited for unidirectional as well as for bidirectional detector pairs. In contrast, in Compton cameras, the Compton angle is used frequently, $$\vartheta = \cos^{-1}\left(1 - \frac{mc^2}{E2} + \frac{mc^2}{E1 + E2}\right) \tag{24}$$

with $mc^2$=511 keV, the rest energy of the electron.

Eq. (2), however, in not an allowable function f(E1,E2) within the meaning of the invention, because $\vartheta$(E1) is not clearly defined over the entire interval 0≤E1≤C.

A coincidence event is sorted according to its value f(E1,E2) into that histogram, which belongs to the detector pair i in which the coincidence has occurred. The entirety of the histograms for all detector pairs i=1, . . . , I forms the two-dimensional frequency distribution $\underline{Y}$, which is constantly filled during a measurement.

Now, the direction distribution $\underline{X}$ of the radiation sources is determined from the recorded frequency distribution $\underline{Y}$.

Corresponding to the experimental situation, two cases are distinguished. With respect to the 3-dimensional direction measurement, the direction distribution is modelled on the celestial sphere from a function X(ω, h) dependent on two variables. The celestial sphere is a sphere commonly used in astronomy and in navigation, by means of which the positions can be determined in the sky. It is an imaginary sphere surrounding the measurement device from all sides, onto which the radiation sources may be projected. The functional value X(ω, h) describes the radiation intensity in a solid angle segment dΩ on the celestial sphere in the azimuth direction w at a height angle h.

For the 2-dimensional direction measurement, a function X(ω) dependent on a variable is considered along the horizontal circle. The functional value X(ω) describes the radiation intensity in the direction of ω. It is assumed that the sources are lying within the same plane, as well as the detectors of the measurement device.

The task of the algorithm is to determine the functions X(ω, h) and X(ω), respectively.

The spatial direction distribution X(ω, h) of the radiation field (and X(ω) in the 2-dimensional case, respectively) may now be calculated by means of arbitrary statistical image reconstruction methods, as they are known from emission tomography. The statistical image reconstruction methods allow for a uniform processing of the measurement data of the entire measurement device, independent of the detector pair being unidirectional or bidirectional.

The common statistic image reconstruction methods comprise, amongst others:
Maximum Likelihood Expectation Maximization (MLEM) Algorithm
Ordered Subset Expectation Maximization (OSEM) Algorithm
List Mode—Maximum Likelihood Expectation Maximization (LM-MLEM) Algorithm
List Mode—Ordered Subset Expectation Maximization (LM-OSEM) Algorithm All methods mentioned above are examples for algorithms, the application field of which is not limited to medicine. By means of the procedure mentioned above, they may be used without further ado in ABC and radiation protection, too.

In the following, the method according to the invention is described in further detail by means of embodiments and with respect to the drawings. The explanations are only exemplary and do not delimit the general spirit of the invention.

According to a further preferred embodiment of the method according to the invention, the radiation sources emit a discrete and/or continuous distribution of the radiation.

According to a further preferred embodiment of the method according to the invention, the radiation sources image emit gamma, electron, positron, proton, ion, and/or neutron radiation.

According to a further preferred embodiment of the method according to the invention, the radiation originates from the radioactive decay of one or more radio nuclides, and/or the radiation is prompt gamma radiation, which is generated during the absorption of proton or ion radiation in target materials.

According to a further preferred embodiment of the method according to the invention, the radiation has a lower intensity, as this is the case, for example, in astronomy.

According to a preferred embodiment of the method according to the invention, the latter comprises in step a), additionally or partially, the following sequence of steps:
calibrating the signals of all detectors as observed radiation energy E;
determining a suitable coordinate system;
acquiring the directions of the defined detector pairs, wherein in the 2-dimensional direction measurement, the direction of the detector pair i is detected with the azimuth angle $\varphi_i$ and wherein in the three-dimensional direction measurement, the direction of the detector pair i is detected with the azimuth angle $\varphi_i$ and the height angle $\beta_i$;
subdividing the measurement range for the functional value f(E1,E2) into a number J of equidistant measurement value channels j=1, . . . , J;
creating one or more two-dimensional arrays with I·J fields as data structures for storing the frequency distributions $\underline{Y}$ in which coincidence events are registered corresponding to their ID number i and their measurement value channel j; a separate two-dimensional array $\underline{Y}$ is created for each radio nuclide;
subdividing the detector pairs i into symmetry classes SK, wherein those detector pairs i, which are mapped during the rotation or translation onto other structurally identical detector pairs are aggregated into one symmetry class SK(i) respectively;
creating one or more lookup tables $LUT^{SK}$ for each symmetry class SK and each radio nuclide, wherein these cover an angle range $\vartheta$ from 0° to 180° and are subdivided into equidistant angle steps;
creating the lookup tables $LUT^{SK}$ by measurements with the detector system, or by Monte Carlo simulations, or by means of a theoretical model;
transferring all lookup tables $LUT^{SK}$ for all the symmetry classes and all the radio nuclides to an algorithm of the image reconstruction, which processes the measurement data and calculates the direction distributions $\underline{X}$.

Preferably, each radiation detector of a measurement device is calibrated for energy measurement. For radiation detectors from the group of medium to high atomic number, the photoelectric effect may be used for energy calibration. For such detectors, the energy calibration is carried out by means of the photo peak in the pulse height spectrum. The procedure is well known to the person skilled in the art in the field of radiation detectors, and will not be further discussed here.

For detectors from the group of lower atomic number, the energy measurement, however, is less common, because the latter usually is operated in pulse counting mode. Several calibration options for detectors with $Z_{eff} \leq 30$ are available. The pulse height spectra of the detectors may also be examined with respect to the presence of photo peaks. If photo peaks are detectable, these may be used for the energy calibration. If no photo peaks are detectable, the final product of the Compton energy spectrum is a suitable, alternative. The maximum energy $E_{C,max}$ observed in Compton scattering events, which also is referred to as the Compton edge, is $$E_{C,max} = \frac{E_\gamma}{1 + \frac{mc^2}{2E_\gamma}} \tag{25}$$

from the radiation energy $E_\gamma$ of the respective radio nuclide, with $mc^2=511$ keV, the rest energy of the electron. The position of the Compton edge may be determined experimentally by forming the first derivation of the pulse height spectrum. The minimum of the first derivation of the pulse height spectrum is a good approximation to the Compton edge. Then, the pulse height at the minimum may be calibrated according to eq. (3) as energy.

Many of the common radiation detectors do not provide information on the interaction point of the radiation in the detector material. Therefore, it is necessary to make an assumption concerning the connection line, which connects the two interaction points in a detector pair with each other. An obvious assumption is to select the line, which connects the centers of the active detector media (the scintillator or the semiconductor) for this. For each detector pair, then, there is a connection line, which runs through both detector centers.

The connection line of a detector pair is considered as a directed quantity. A vector is assigned to the line. The vector has its origin in the center of detector 2, and points to the center of detector 1.

Now, the directions of the detector pairs in space should be determined. Thereby, a parallel radiation onto the measurement device is assumed (far field). The incident radiation is approximately parallel, if the distances of all radiation sources are much larger than the dimensions of the measurement device.

At first, a suitable coordinate system has to be determined, which is applicable for the radiation sources as well as for the radiation detectors. With respect to the 3-dimensional direction measurement, this is a spherical coordinate system, wherein the coordinate origin is the spatial center of the detector arrangement. In the 2-dimensional case, a polar coordinate system is used.

It is to be assumed that the coordinate system can be displaced in space parallel to the axes of the Cartesian coordinate directions. For each detector pair, the coordinate system may thus be displaced respectively to the center of detector 2.

At first, the 3-dimensional case is examined: the spherical coordinates of detector 1 in this displaced coordinate system, the origin of which respectively lies in detector 2, define a characteristic azimuth and height angle for this detector pair. Each detector pair i thus comprises such a characteristic azimuth angle $\varphi_i$ and height angle $\beta_i$. Both angles $\varphi_i$ and $\beta_i$ associated with the detector pair are stored in the software. They are used in the analysis methods.

In the 2-dimensional case, this is a polar coordinate system, which is displaced for each detector pair i parallel to the axes of the Cartesian coordinate directions respectively into the center of detector 2. The azimuth angle $\varphi_i$ of detector 1 in this displaced coordinate system is stored in a software for each detector pair i.

As further components, the method according to the invention uses a system matrix, which describes the response behavior of the device as a point radiation source. Because the computing expense of the data processing is scaled to the size of the system matrix, it is helpful to use the symmetry properties of the measurement device, in order to keep the system matrix as small as possible. For this, the detector pairs of a measurement device are categorized into symmetry classes.

Those detector pairs, which are mapped to other detector pairs of similar design upon rotation or displacement, belong to one symmetry class. They are aggregated into one group and are all treated in the same way. The system matrix is defined as a group of lookup tables. Each lookup table describes the response behavior of detector pairs of these symmetry classes for respectively one symmetry class with respect to a point radiation source that is infinitely far away. The lookup tables may be derived by means of a simulation calculation, a theoretical model, or from measurements using point reference radiators.

For each symmetry class and each radio nuclide, there is a lookup table. The entirety of all lookup tables forms the system matrix of the measurement device. Thereby, the lookup tables represent the mathematical relationships between the radiation sources and the measurement data.

The elements of a lookup table are functions of representation $LUT_j[\vartheta]$. They represent the probabilities that a radiation source and an angle $\vartheta$ with respect to the detector pair axis causes coincidence events in bins j of the measurement value distribution f(E1, E2). The index j indicates the $j^{th}$ class of the measurement value distribution f(E1, E2).

According to a further preferred embodiment of the method according to the invention, in step a) the lookup tables $LUT^{SK}$ are created by measurements by means of the detector system by carrying out the following sequence of steps:

creating a prescription for creating and validating the lookup tables $LUT^{SK}$ from reference measurements, which select the reference sources, consider the type of nuclide, as well as define the measurement conditions by means of which the measurements are to be carried out;

performing reference measurements for all steps previously defined in the prescription;

creating and validating the lookup tables $LUT^{SK}$ according to the previously defined prescription for analyzing the measurement data from the reference measurements;

acquiring the natural background radiation $b^{SK(i)}$ for all the symmetry classes SK;

excluding the natural background radiation $b^{SK}$ from the lookup tables $LUT^{SK}$;

In the following, an embodiment of the invention is described with respect to how the lookup tables are created experimentally by means of point-shaped reference emitters. All reference emitters should be spaced apart from the measurement device far enough for the radiation being incident on the device almost parallel (far field).

It is an advantage to perform the measurements by means of several reference sources of different nuclides. The sources should be selected such that they represent the energy range in which the measurement device is used. The distance of the sources should be large enough in order to ensure parallel radiation. Ideally, the distance is selected as large as is allowable by the intensity of the source in order to gain measurement data in reasonable acquisition times.

For each source, a series of several measurements is carried out at different angular positions. It should be taken care of the source always having the same radial distance with respect to the center of the device during all measurements. All of the measurements are carried out for the same measurement time t. The data acquisition should take place under the same conditions, as they are also provided for the actual operation.

If the implementation requirements of the measurement device provide for providing not only relative intensities but rather also absolute radiation intensities in measurement units of, e.g., pGy sr$^{-1}$ s$^{-1}$ or nSv sr$^{-1}$ h$^{-1}$, it should be taken care of only calibrated reference emitters being used.

In other cases, it is sufficient if the data of the lookup table is acquired with constant relative radiation intensity; then, an absolute calibration of the radiation intensity is not required. Then, sources of any intensity may be used, as far as their activity is sufficient for good counter statistics.

After completing the measurements by means of the reference sources, in a further measurement, the background radiation should be detected in a further measurement without a source. The background measurement should be carried out for the same measurement period t as the measurements that have been carried out previously with the reference sources.

The procedure for obtaining the lookup tables from the measurement data is identical for all nuclides, and here, only one nuclide is described exemplarily.

It is assumed that all detector pairs have been classified into the symmetry classes. Each symmetry class has an identification number SK(i), which is to be defined for each detector pair i.

For each symmetry class, a separate lookup table $LUT^{SK}$ is created, which covers the angle range from 0° to 180° and subdivides it into equidistant angular sections.

The data recorded at a certain angular position has to be analyzed for each detector pair. According to the current position of the reference source at an azimuth angle ω and a height angle h, the angular distance $\vartheta_i$ is calculated for each detector pair i:

$$\vartheta_i = \arccos(\cos \beta_i \cos h \cos(\omega - \varphi_i) + \sin \beta_i \sin h) \quad (26)$$

In the expression mentioned above, $\varphi_i$ indicates the azimuth angle and $\beta_i$ the height angle of the detector pair i. In the 2-dimensional case, the angle distance $\vartheta_i$ may be calculated according to $$\vartheta = \arccos(\cos(\omega - \varphi_i)) \quad (27)$$

The procedure is repeated for all angle positions of the reference source.

Now, the measurement data is sorted according to the affiliation of the detector pairs to symmetry classes, in order to create the lookup tables therefrom. For all pairs i of a symmetry class (i), the measurement values are available at the angular distances $\vartheta_i$.

The aim is to fill up the corresponding table $LUT^{SK}$ for each symmetry class SK with data over the entire range of values from $\vartheta 9=0°$ to 180°.

For each value $\vartheta$ from the range from $\vartheta=0°$ to 180, now, the data set $\vartheta_i$ of a symmetry class SK is selected respectively, which is closest to the current value $\vartheta$. This data set is copied to the location of $\vartheta$ of the lookup table. This procedure is continued until all positions $\vartheta$ from 0° to 180° of a lookup tables are filled with data. The procedure is to be carried out for all the symmetry classes. According to this procedure, the lookup tables of a measurement device are created.

The measurement without a reference source serves for measuring the natural radiation background. The natural radiation background may be assumed as being isotropic. All background data sets belonging to the same symmetry class may be averaged. The average data set is indicated by $b_j^{SK}$ and is applicable for all detector pairs of a symmetry class SK.

The radiation background comprised in the lookup tables may be subtracted by subtracting the background $b_j^{SK}$ in the bin j of the measurement value distribution f(E1, E2) from each element of the table $LUT_j^{SK}(\vartheta)$.

The central component of the method according to the invention is the recorded lookup tables. Lookup tables are energy specific and respectively are applicable for the characteristic radiation energy of the radiation source. For setting up a measurement device for certain operating conditions, various options are possible. If the intended use is coupled to a manageable number of nuclides, it may be reasonable to create a set of lookup tables for each nuclide. If, on the other hand, the measurement device is to be used in a wide energy range with very different nuclides, it is advantageous to perform a further stage of data processing. The lookup tables may be fitted by functions. The fitting parameters are acquired from different gamma energies and are stored as energy dependent functions. During a measurement, lookup tables for arbitrary gamma energies may be created from the stored energy dependent functions. Thus, the device may be adapted dynamically to the currently prevailing situations. Radiation sources may be mapped over a wide energy range.

According to a further preferred embodiment of the method according to the invention, in step e), a selection requirement with respect to the energy sum E1+E2 of the energies detected in both detectors of a pair is applied. If there are several radio nuclides, in the embodiments, selection requirements are used in order to create in step e) a separate frequency distribution Y for each radio nuclide, and/or in step f) a separate direction distribution X for each radio nuclide.

For acquiring the two-dimensional frequency distribution Y, it is recommended to make a selection of the coincidence events by means of a selection requirement for the energy sum E1+Ex. Only such values f(E1, E2) should be sorted into the distribution Y, the energy sum E1+E2 of which lies within a predefined region around the energy value, which corresponds to the characteristic nuclide energy, the radiation of which is detected. By means of such a selection requirement it is possible to analyze separate frequency tables for each nuclide.

According to a further preferred embodiment of the method according to the invention, in step e), several selection requirements with respect to the energy sum E1+E2 are applied for radio nuclides with several gamma energies, and/or for such radio nuclides with several gamma energies, one or more frequency distribution Y are created.

If the directions of sources of a nuclide are measured, which emits radiation on several lines, it is up to the user, whether the coincidence events are to be acquired in one or in several frequency distributions. For example, Co-60 has two lines lying close to each other at 1173 keV and 1332 keV. Coincidence events of both emissions may be sorted into the same frequency distribution without any problems. Because both emission lines are lying that close to each other, also the 2-dimensional frequency distributions are very similar, and may be analyzed together without difficulties. If, however, a nuclide has several gamma lines that are lying far a way from each other, it is recommendable to acquire these separately. The frequency distributions belonging to a nuclide are merged later on again in the analysis process.

According to a further preferred embodiment of the method according to the invention, the statistical image reconstruction method in step f) partially or completely is the Maximum Likelihood Expectation Maximization (MLEM) method, the Ordered Subset Expectation Maximization (OSEM) method, the List Mode-Maximum Likelihood Expectation Maximization (LM-MLEM) method, and/or the List Mode-Ordered Subset Expectation Maximization (LM-OSEM) method.

In the following, two embodiments of the invention are described, as to how a spatial direction distribution X(ω, h)

and a planar direction distribution $X(\omega)$ may be calculated by means of the Maximum Likelihood Expectation Maximization (MLEM) algorithm. The explanations are applicable for devices, in which the sum $\Sigma_{i,j} Y_{ij}$ of all inputs in the frequency distribution $\underline{Y}$ do not have a direction dependency. If many detector pairs are present, the direction dependency of individual detector pairs is averaged; then the total counting rate $\Sigma_{i,j} Y_{ij}$ is approximately independent of the direction.

According to a further preferred embodiment of the method according to the invention, in step f), a 3-dimensional direction distribution $X_{kl} = X(\omega_k, h_l)$ is calculated for each detected radio nuclide according to $$X_{kl}^{[n+1]} = X_{kl}^{[n]} \frac{KL}{\Sigma Y_{ij}} \sum_{i,j} \frac{LUT_j^{SK(i)}[\vartheta(\omega_k, h_l, \varphi_i, \beta_i)] Y_{ij}}{\sum_{k'=1}^{K} \sum_{l'=1}^{L} LUT_j^{SK(i)}[\vartheta(\omega_{k'}, h_{l'}, \varphi_i, \beta_i)] X_{k'l'}^{[n]}}$$

from the initial distribution $\forall k=1, \ldots, K, l=1, \ldots, L \; X_{kl}^{[0]} = 1$ using the lookup tables $LUT^{SK}$ and Euler distance function according to $\vartheta(\omega_k, h_l, \varphi_i, \beta_i) = \arccos(\cos \beta_i \cos h_l \cos(\omega_k - \varphi_i) + \sin \beta_i \sin h_l)$ wherein K and L are numbers of pixels for the azimuth angle $\omega_k$ and the height angle $h_l$ defined by the user.

In the following, an algorithm for the reconstruction of a three-dimensional direction distribution is described. Firstly, the surface of a celestial sphere is divided into degrees of latitude and longitude. Each one of the equally dimensioned area elements on the celestial sphere corresponds to an image pixel (k,l) for which the radiation intensity $X_{kl} = X(\omega_k, h_l)$ ab the azimuth angle $\omega_k$ and the height angle $h_l$ should be calculated. It should be taken care of the classes for the height angle $h_l$ being selected such that the sine of the height angle is evenly distributed in the interval (−1,1). In total, there are K·L pixels $X_{kl}$ for K classes $\omega_k$ and L classes $h_l$.

Maximum Likelihood Expectation Maximization (MLEM) is an iterative method that requires the direction distribution $\underline{X}$ for the initial values:

$\forall k=1, \ldots, K, l=1, \ldots, L \; X_{kl}^{[0]} = 1$ (28)

The MLEM iteration prescription for calculating a new representation $X_{kl}^{[n+1]}$ from the previous values $X_{kl}^{[n]}$ is expressed by:

$$X_{kl}^{[n+1]} = X_{kl}^{[n]} \frac{KL}{\Sigma Y_{ij}} \sum_{i,j} \frac{LUT_j^{SK(i)}[\vartheta(\omega_k, h_l, \varphi_i, \beta_i)] Y_{ij}}{\sum_{k'=1}^{K} \sum_{l'=1}^{L} LUT_j^{SK(i)}[\vartheta(\omega_{k'}, h_{l'}, \varphi_i, \beta_i)] X_{k'l'}^{[n]}} \quad (29)$$

Herein, $Y_{ij}$ indicates the counters (the measurement values) for a detector pair i in the bin j of the measurement value distribution f(E1, E2) registered in the frequency table $\underline{Y}$. When invoking the lookup tables $LUT^{SK(i)}$, the angular distance $\vartheta$ between a pixel (k,l) on the celestial sphere and a detector pair i is to be calculated. In a three-dimensional case, the angular distance $\vartheta$ may be calculated according to $\vartheta(\omega_k, h_l, \varphi_i, \beta_i) = \arccos(\cos \beta_i \cos h_l \cos(\omega_k - \varphi_i) + \sin \beta_i \sin h_l)$ (30)

wherein $\varphi_i$ is the azimuth angle and $\beta_i$ the height angle of the detector pair i.

The MLEM algorithm is a method, which uses a frequency distribution, namely, the measured frequency distribution $\underline{Y}$, which indicates how frequently coincidences have occurred in certain detector pairs at certain measurement values, and which calculates a new frequency distribution therefrom, namely, the direction distribution $\underline{X}$, that is searched, which indicates, at which frequency the radiation is incident on the detection site with certain angles of incidence $\omega_k$ and $h_l$.

Equation (7) is formulated such that the iteration prescription may be carried out in parallel to the data acquisition, while coincidence counters $Y_{ij}$ are accumulated continuously in the frequency distribution $\underline{Y}$.

According to a further preferred embodiment of the method according to the invention, in step f) for each detected radio nuclide, a two-dimensional direction distribution $X_k = X(\omega_k)$ is calculated according to $$X_k^{[n+1]} = X_k^{[n]} \frac{K}{\Sigma Y_{ij}} \sum_{i,j} \frac{LUT_j^{SK(i)}[\vartheta(\omega_k, \varphi_i)] Y_{ij}}{\sum_{k'=1}^{K} LUT_j^{SK(i)}[\vartheta(\omega_{k'}, \varphi_i)] X_{k'}^{[n]}}$$

from the initial distribution $\forall k=1, \ldots, K \; X_k^{[0]} = 1$ using the lookup tables $LUT^{SK}$ and an angular distance function according to $\vartheta(\omega_k, \varphi_i) = \arccos(\cos(\omega_k - \varphi_i))$ wherein K is a number of pixels for the azimuth angle $\omega_k$ defined by the user.

According to a further embodiment of the invention, a planar direction distribution $X_k = X(\omega_k)$ may be calculated by means of the MLEM algorithm. An initial distribution is initialized $\forall k=1, \ldots, K \; X_k^{[0]} = 1$ (31)

and an iteration loop with the iteration prescription:

$$X_k^{[n+1]} = X_k^{[n]} \frac{K}{\Sigma Y_{ij}} \sum_{i,j} \frac{LUT_j^{SK(i)}[\vartheta(\omega_k, \varphi_i)] Y_{ij}}{\sum_{k'=1}^{K} LUT_j^{SK(i)}[\vartheta(\omega_{k'}, \varphi_i)] X_{k'}^{[n]}} \quad (32)$$

is performed. The angular distance $\vartheta$ is calculated in the 2-dimensional case according to $\vartheta(\omega_k, \varphi_i) = \arccos(\cos(\omega_k - \varphi_i))$ (33)

The direction distribution $\underline{X}$ of the radiation field, at first, is unit-less. The values $X_{kl}$ represent the relative radiation intensities in different directions of incidence $\omega_k$ and $h_l$. However, it is also possible to indicate the radiation intensity by means of the measuring unit of a dose rate per spatial angle. For this, it is necessary to firstly adapt the detector system such that nuclide specific dose rates can be measured.

For the measurement of nuclide specific dose rates, counting rates of interaction events are used, the total energy of which corresponds to the respective nuclide energy. Thereby, various options are available. On the one hand, nuclide specific counting rates of all detectors of medium to high atomic numbers comprised in the device may be used, on the other hand, also counting rates of coincidence events may be used, the total energy E1+E2 of which lies in a specific interval around the nuclide energy. These counting rates may be calibrated in units of the equivalent dose rate or in units of the absorbed dose rate (in air). Here, this procedure will be briefly explained.

The calibration is carried out by means of a reference source with calibrated activity $\Lambda$. The dose rate $\dot{D}$ and the equivalent dose rate $\dot{H}^*(10)$, respectively, and the center of the device may be calculated from the activity $\Lambda$ of the source, its distance r and the nuclide specific dose rate constant $\Gamma$ and $\Gamma_H$, respectively. The (physical) dose rate $\dot{D}$ is derived from:

$$\dot{D} = \frac{dD}{dt} = \frac{\Lambda \Gamma}{r^2} \tag{34}$$

and the equivalent dose rate $\dot{H}^*(10)$ from:

$$\dot{H}^*(10) = \frac{dH^*(10)}{dt} = \frac{\Lambda \Gamma_H}{r^2} \tag{35}$$

The values of the dose rate constant $\Gamma$ and the equivalent dose rate constant $\Gamma_H c$ for the various nuclides can be found in tables of relevant literature.

One counting rate or a combination of counting rates now has to be selected from the counting rates available for nuclide specific counting rates of the device, which, while avoiding the systematic errors, is suitable for representing the dose rate. A possible cause for systematic errors during the measurement of the dose rate is a non-uniform response behavior of the device with respect to the direction of the incident radiation. The counting rates, for example, may be affected by shadowing effects. In particular, the coincidence counting rates are characterized by their strong direction dependency. The direction and sensitivity of the coincidence events that is advantageous for the direction measurement may be a substantial error cause during the measurement of the dose rate.

In the following, two embodiments of the invention are presented, as to how a measurement of nuclide specific dose rates is possible with small systematical errors.

For devices, for which shadowing effects are negligible, it is reasonable to consider the nuclide specific counters $N_m$ in the photo peak detected in the detectors m=1, . . . , M with high atomic number. The counting rate $\dot{Z}$, defined as:

$$\dot{Z} = \frac{d(\text{Max}(N_1, \ldots, N_M))}{dt} \tag{36}$$

may be a good measure for the dose rate, if there is at least one detector of high atomic number in each direction, which is exposed to the incident radiation unobstructedly.

An alternative procedure is offered for all devices, which consist of many detectors. Here, the sum of all coincidence counters in the frequency distribution $\underline{Y}$ may serve as measure for the absorbed dose, provided that the total counting rate $$\dot{Z} = \frac{d\left(\sum_{i,j} Y_{ij}\right)}{dt} \tag{37}$$

is direction independent.

The suitability of a certain variable $\dot{Z}$ for the calibration of the dose rate can be checked by moving a reference source in a constant distance r around the device. If the counting rate $\dot{Z}$ remains constant, while the source is moved around the device, the requirement is met. The variable $\dot{Z}$ may then be used for the calibration of the dose rate.

For the calibration of the dose rate by means of the counting rate $\dot{Z}$ a background measurement is recorded without a source. The thus determined counting rate is referred to as $\dot{Z}_b$. Now, device specific calibration constants C and $C_H$ may be defined, by means of which the dose rate $\dot{D}$ $$\dot{D} = C(\dot{Z} - \dot{Z}_b) \tag{38}$$

and the equivalent dose rate $\dot{H}^*(10)$ $$\dot{H}^*(10) = C_H(\dot{Z} - \dot{Z}_b) \tag{39}$$

may be calculated from the background corrected counting rate $\dot{Z} - \dot{Z}_b$.

Now, by means of the device specific calibration constants C and $C_H$, direction-independent dose rates per spatial angle may be calculated. For this, the intensity values $X_{kl}$ are multiplied by a scaling factor. In the following, it is assumed that the counting rate $\dot{Z}$ according to eq. (15) and the calibration constants C and $C_H$ according to eq. (16) and (17), respectively, are defined.

The dose rate $\dot{D}$ per spatial angle $d\Omega$ is calculated by $$\frac{dD(\omega_k, h_l)}{dtd\Omega} = \frac{C(\dot{Z} - \dot{Z}_b)}{4\pi} X_{kl} \tag{40}$$

The equivalence dose rate $\dot{H}^*(10)$ per spatial angle $d\Omega$ by:

$$\frac{dH^*(10)(\omega_k, h_l)}{dtd\Omega} = \frac{C_H(\dot{Z} - \dot{Z}_b)}{4\pi} X_{kl} \tag{41}$$

In the 2-dimensional case, $$\frac{dD(\omega_k)}{dtd\omega} = \frac{C(\dot{Z} - \dot{Z}_b)}{2\pi} X_k \tag{42}$$

applies, and:

$$\frac{dH^*(10)(\omega_k)}{dtd\omega} = \frac{C_H(\dot{Z} - \dot{Z}_b)}{2\pi} X_k \tag{43}$$

For the dose rate range up to 1 µSv/h, the (physical) dose rate per spatial angle may be specified, for example, by the measurement unit pGy sr$^{-1}$ s$^{-1}$. The equivalence dose rate per spatial angle may be measured, for example, in units of nSv sr$^{-1}$ h$^{-1}$.

If the dose rate per spatial angle is averaged over all directions of incidence, the dose rate $\dot{D}$ is obtained, which is received from all directions, divided by $4\pi$. The same applies for the equivalent dose rate: the equivalent dose rate per spatial angle averaged over all directions of incidence is equal to the equivalent dose rate $\dot{H}^*(10)$, divided by $4\pi$.

Further, the invention relates to a device for carrying out to the method according to the invention, wherein the device according to the invention, hereby, comprises a group of several synchronized detectors for detecting of radiation, wherein at least one detector material has an atomic number of $Z_{eff} > 30$ and all detectors measure the energies E, which occur in interactions of the radiation with the detector materials.

Further, the device according to the invention comprises a system electronics, which registers coincidence events, if interactions take place in respectively two detectors from a list of defined detector pairs i simultaneously, wherein the list of defined detector pairs comprises all pairs, which may be formed in combination from the quantity of all detectors, and wherein the defined detector pairs comprise at least one detector from a material having an atomic number of $Z_{eff} > 30$.

The device according to the invention comprises a data acquisition system, which determines a ranking for both detectors involved in a coincidence event, which defines a first and a second detector, and sorts the energies (E1, E2) measured in the coincidence events corresponding to their indication 1, 2, and stores them in a chronological list with the attributes {i, E1, E2} and the detection time t; wherein, in each detector pair i the detector having the lower atomic number receives the number 1, and that one having the higher atomic number receives the number 2; wherein if both detectors of the pair should have the same atomic number, the indication 1 and 2, respectively, is made arbitrarily.

Moreover, the device according to the invention comprises an analysis unit, which creates one or more frequency distributions $\underline{Y}$ from the data stored in the data acquisition system, wherein a function f(E1, E2) is applied, which is dependent on two energy values (E1, E2) and this function f(E1, E2) is traceable back to a function f(E1) when substituting E2 by C−E1, which function is clearly defined, constant, and monotonous over the entire interval [0,C], wherein C is a constant, which represents the radiation energy C=E1+E2, and wherein the analysis unit reconstructs one or more direction distributions $\underline{X}$ of the radiation field.

According to a further preferred embodiment of the device according to the invention, the latter is configured partially or completely as a Compton camera, a Compton telescope, a single plane Compton camera, a neutron camera, and/or a dual gamma/neutron camera.

A device within the meaning of the invention is also assumed as being a measurement device, in short, a device or a detector system.

According to a further preferred embodiment of the device according to the invention, the entirety of all detectors of the device has an annular design, according to which the detectors are arranged in a ring, and/or wherein in the interior of the ring, there is no, one, or several central detectors.

Further, the ring preferably comprises four or five and specifically preferred six plastic scintillation detectors. Further, preferably one or two scintillation detectors from NaI, CsI, CeBr$_3$ and/or LaBr$_3$ are provided in the interior of the ring.

According to a further preferred embodiment of the device according to the invention, the latter preferably is formed by scintillation detectors having a size of 1"×1", 1.5"×1.5", 2"×2" and/or 3"×3".

According to a further preferred embodiment of the device according to the invention, a scintillation detector is used as detector, and/or the scintillator is configured as monolithic block or as pixelated scintillator module, and/or is formed from pure or doped materials from the group of PVT, anthracene, stilbene, p-terphenyl, CaF$_2$, BaF$_2$, NaI, CeBr$_3$, LaBr$_3$, LaCl$_3$, La(Br$_x$Cl$_{1-x}$)$_3$, CsI, SrI$_2$, CLYC, CLBC, CLCB, CLLB, BGO, LSO, LYSO, GAGG, YAP and/or YAG.

According to a further preferred embodiment of the device according to the invention, the detector is used as semiconductor detector, and/or the semiconductor is formed as segmented or non-segmented semiconductor, and/or has a planar or coaxial geometry, and/or is formed from materials of the group of Ge, GaAs, CdTe and/or CdZnTe.

According to a further preferred embodiment of the device according to the invention at least two detectors are used.

According to a further preferred embodiment of the device according to the invention, all detectors used basically are similar in construction, or at least two of the detectors used are different to each other.

According to a further preferred embodiment of the device according to the invention, a detector and system electronics is used, which uses analog and/or digital electronic components. Thereby, the analog electronics components comprise a combination of different modules comprising a high-voltage supply, a preamplifier, an amplifier, a pulse shaper, a charge integrator, a pulse height analyzer, a multichannel analyzer (MCA) and/or a coincidence circuit.

According to a further preferred embodiment of the device according to the invention, the digital electronics components may comprise a combination of various hardware and software components, which comprise a high-voltage supply, an A/D converter per detector, a Field Programmable Gate Array (FPGA), a storage medium, a digital signal processor, and/or an analysis software.

Other details, objects, and advantages of the embodiments of the detection apparatus and detection method will become apparent as the following description of certain exemplary embodiments thereof proceeds.

BRIEF DESCRIPTION OF THE DRAWINGS

The invention and embodiments thereof will be described below in further detail in connection with the drawings. It should be understood that like reference characters used in the drawings may identify like components. In the drawings:

FIG. 4a shows a schematic illustration that is not to scale of a device model with a central cerbromide detector which is surrounded by six plastic detectors that are arranged circularly according to a further embodiment of the invention;

FIG. 4b shows a schematic illustration that is not to scale of a device module according to FIG. 4a in which a further cerbromide detector is included according to a further embodiment of the invention;

FIG. 6a shows a schematic illustration that is not to scale of a first symmetry class of four cube-shaped detectors in total, arranged in a square, wherein two horizontal and two vertical detector pairs are present, according to a further embodiment of the invention;

FIG. 6b shows a schematic illustration that is not to scale of a further symmetry class of four cube-shaped detectors in total arranged in a square of FIG. 6a, according to a further embodiment of the invention;

FIG. 7 shows a schematic illustration of a frequency distribution Y of the device model of FIG. 4b in a 3-dimensional direction measurement according to a further embodiment of the invention;

FIG. 9 is a schematic illustration of a lookup table according to a further embodiment of the invention;

DETAILED DESCRIPTION

Figure 1:
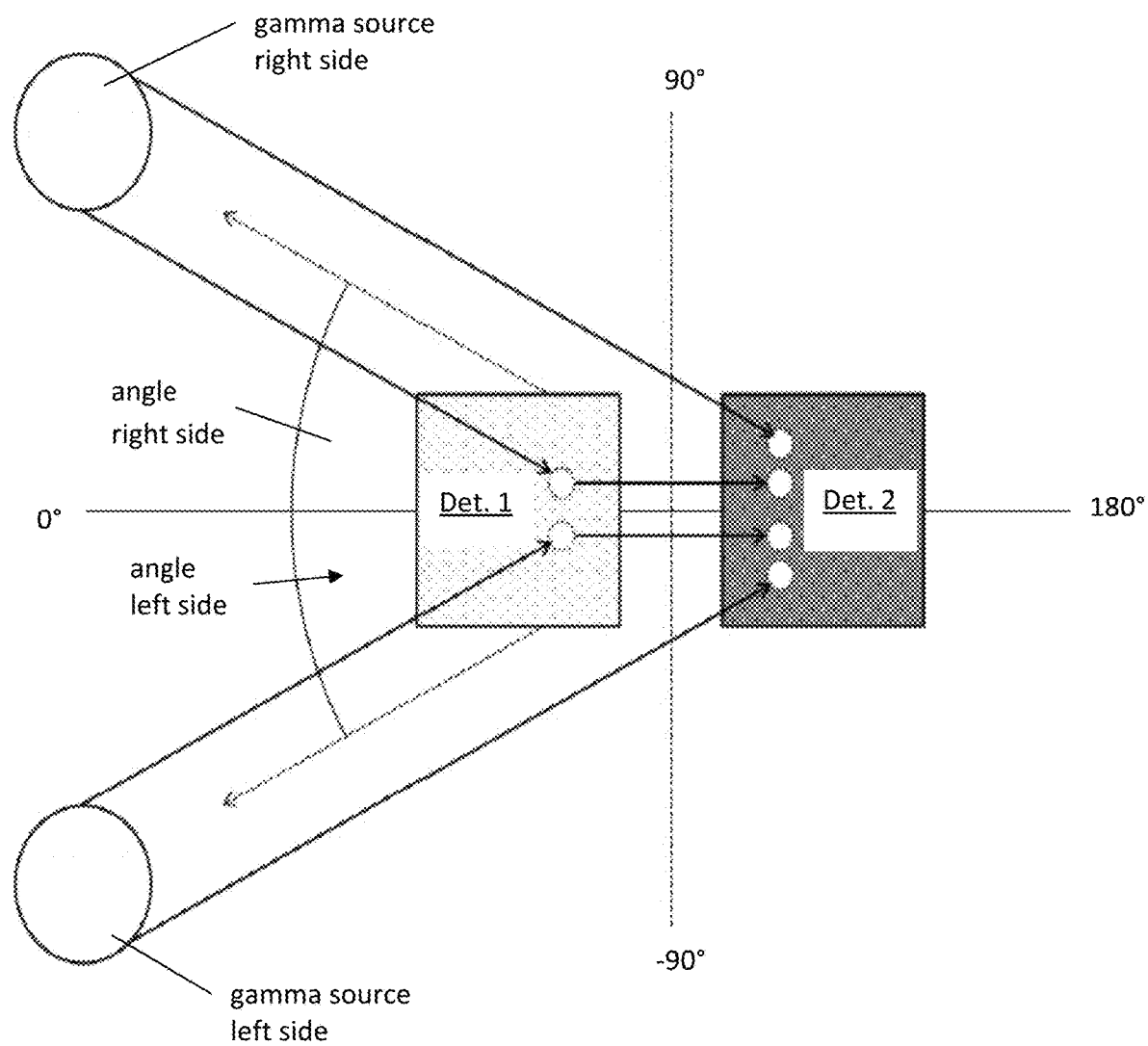
FIG. 1 shows a schematic illustration that is not to scale of a unidirectional detector pair in a 2-dimensional measurement situation according to an embodiment of the invention.

In FIG. 1, a schematic illustration that is not to scale of a unidirectional detector pair is illustrated in a 2-dimensional measurement situation. The detector having an atomic number of $Z_{eff} \leq 30$ is indicated by the number 1, wherein the detector having a higher atomic number of $Z_{eff} > 30$ is indicated by the number 2. The reconstruction of the direction of incidence remains ambiguous. The angle of the incident radiation with respect to the connection line of both detectors can be measured, but not the side, on which the source is located.

Figure 2:
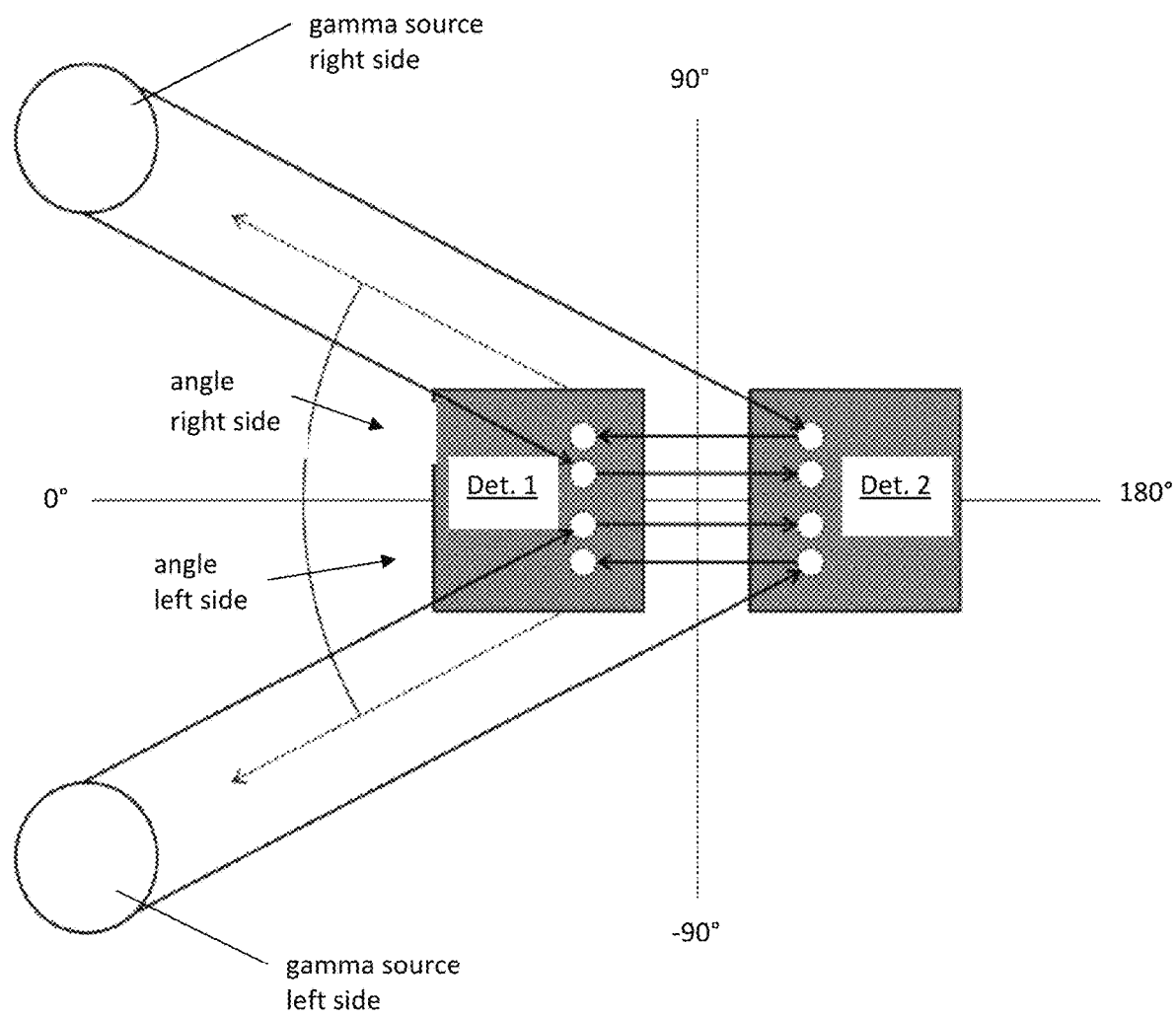
FIG. 2 shows a schematic illustration that is not scale of a bidirectional detector pair in a 2-dimensional measurement situation according to a further embodiment of the invention.

FIG. 2 shows a schematic illustration that is not to scale of a bidirectional detector pair in 2-dimensional measurement situation. Both detectors consist of materials having the same or similar atomic number of $Z_{eff} > 30$. The indication of the two detectors of a bidirectional pair as detector 1 and detector 2 is set once, and then has to be used consistently in all calculations. As with respect to the unidirectional detector pair in FIG. 1, the reconstruction of the direction of incidence remains ambiguous. The angle of the incident radiation with respect to the connection line of both detectors can be measured, however, not the side on which the source is located.

Figure 3:
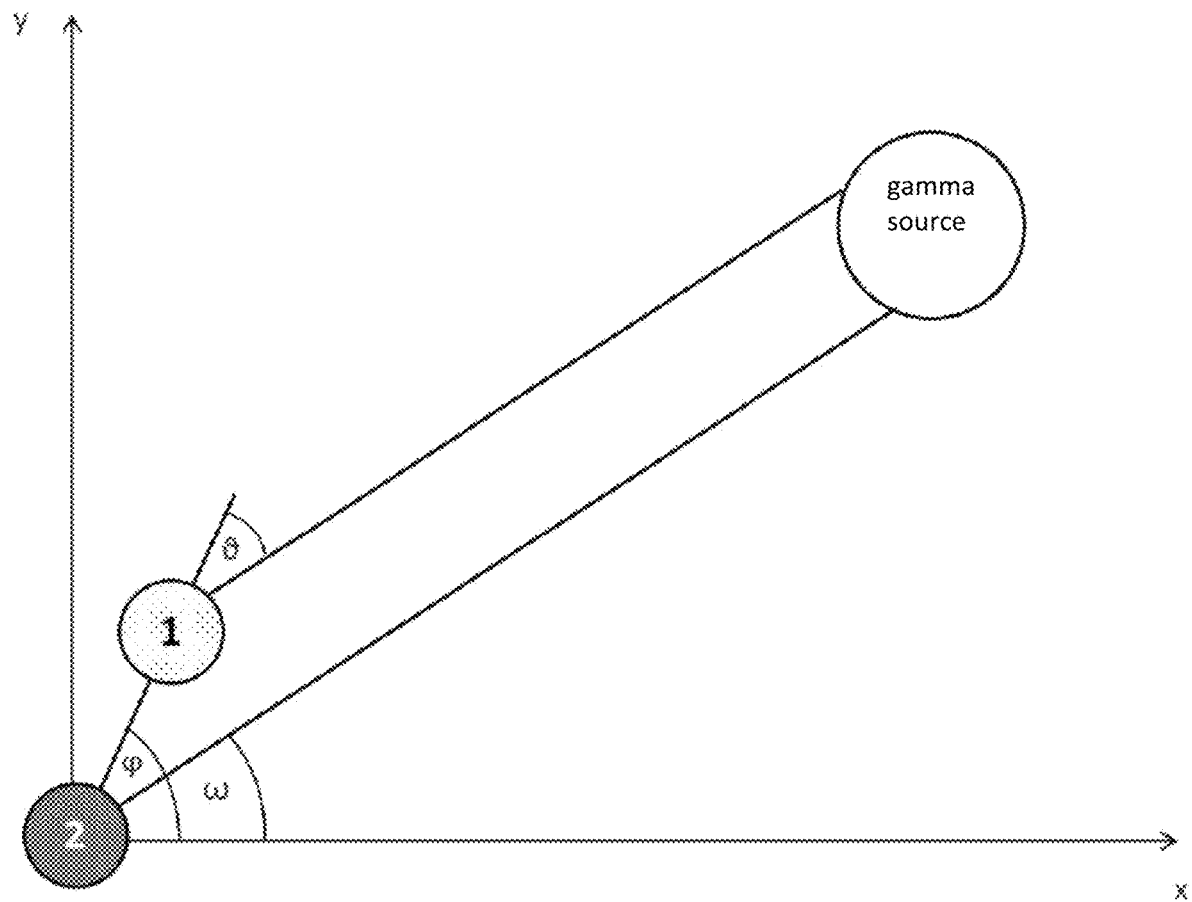
FIG. 3 shows a schematic illustration that is not to scale of the radiation from a source incident on a detector pair 1, 2 in a 2-dimensional measurement situation according to a further embodiment of the invention.

FIG. 3 shows the radiation of a source incident on a detector pair 1, 2 in a 2-dimensional measurement situation.

FIG. 4 shows two device models according to the invention. In the model of FIG. 4a, a central cerbromide detector is surrounded by six plastic detectors circularly. This model is suitable for the 2-dimensional direction measurement. If a further cerbromide detector is arranged below the central cerbromide detector, the model of FIG. 4b is created, which allows for 3-dimensional direction measurements.

Figure 5:
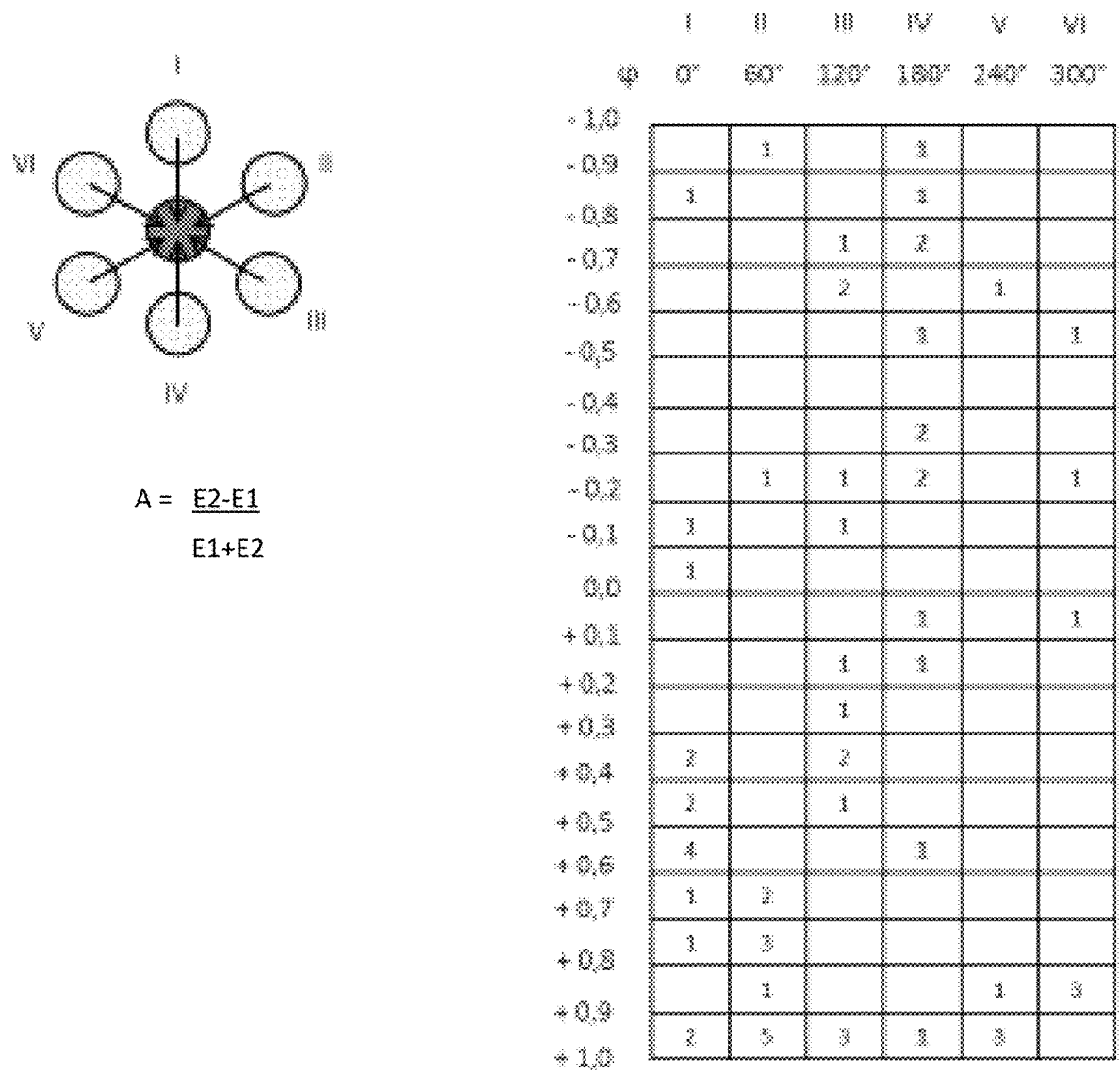
FIG. 5 shows a schematic illustration of a frequency distribution Y of the device model of FIG. 4a in a 2-dimensional direction measurement according to a further embodiment of the invention.

FIG. 5 shows an example for a frequency distribution Y (the measurement data) for the device model of FIG. 4a. The system electronics determines, which detectors have been coincident, and calculates the asymmetry value $A=(E2-E1)/(E1+E2)$ from the coincident energy inputs E1 and E2. The coincidence events are registered according to their detector pair identification number and their asymmetry value A in the frequency distribution Y.

FIG. 6 illustrates how detector pairs are grouped into the symmetry classes. Four cube-shaped detector are arranged in a square. This detector arrangement has two symmetry classes. The first symmetry class is shown in FIG. 6a and comprises two horizontal and two vertical detector pairs. The two diagonal detector pairs, which can be seen in FIG. 6b, form a further symmetry class.

FIG. 7 shows an example for a frequency distribution Y (the measurement data) for the device model of FIG. 4b. The measurement data Y has been grouped corresponding to three symmetry classes of the device model of FIG. 4b into three groups. The detector pairs I to VI belong to the symmetry class 1, the detector pairs VII to XII to the symmetry class 2. The $13_{th}$ detector pair forms an own symmetry class 3.

Figure 8A:
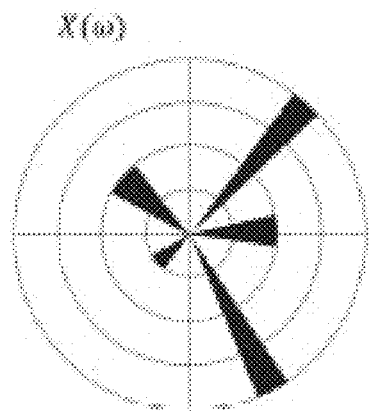
FIG. 8a shows a schematic illustration that is not to scale of a direction distribution for a radiation far field, the emission points of which are on lying within one plane. The direction distribution is modelled along the horizontal circle as a function $X(\omega)$ that is dependent on the azimuth angle $\omega$ according to a further embodiment of the invention.
Figure 8B:
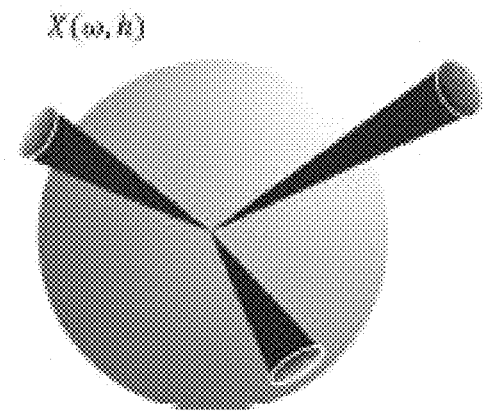
FIG. 8b is a schematic illustration that is not to scale of a direction distribution for a radiation far field, the emission points are distributed in space arbitrarily. The direction distribution is modelled on the celestial sphere as a function $X(\omega, h)$ that is dependent on the azimuth angle $\omega$ and the height angle h according to a further embodiment of the invention.

FIG. 8 shows two schematic illustrations of direction distributions for radiation far fields. A radiation far field is characterized completely by its direction dependency. Depending on the measurement situation, there are two types of distributions. If all radiation sources and the measurement device are lying in one plane, the distribution $X(\omega)$ along the horizontal circle dependent on the azimuth angle $\omega$ is used, as shown in FIG. 8a. The universal direction distribution is the distribution $X(\omega, h)$ on the celestial sphere shown in FIG. 8a, which is dependent on the azimuth angle $\omega$ and the height angle h. The value X represents the radiation intensity. It may be standardized either to the largest value that has occurred, or may be specified by means of a measuring unit.

FIG. 9 shows a lookup table schematically. A lookup table is a 2-dimensional frequency distribution, which determines the coincidence counters as a function of the angular distance $\vartheta$ of a radiation source to the detector pair axis and a measurement value. Here, the measurement value is the energy asymmetry $A=(E2-E1)/(E1+E2)$ of both energy inputs in a coincidence event.

Figure 10:
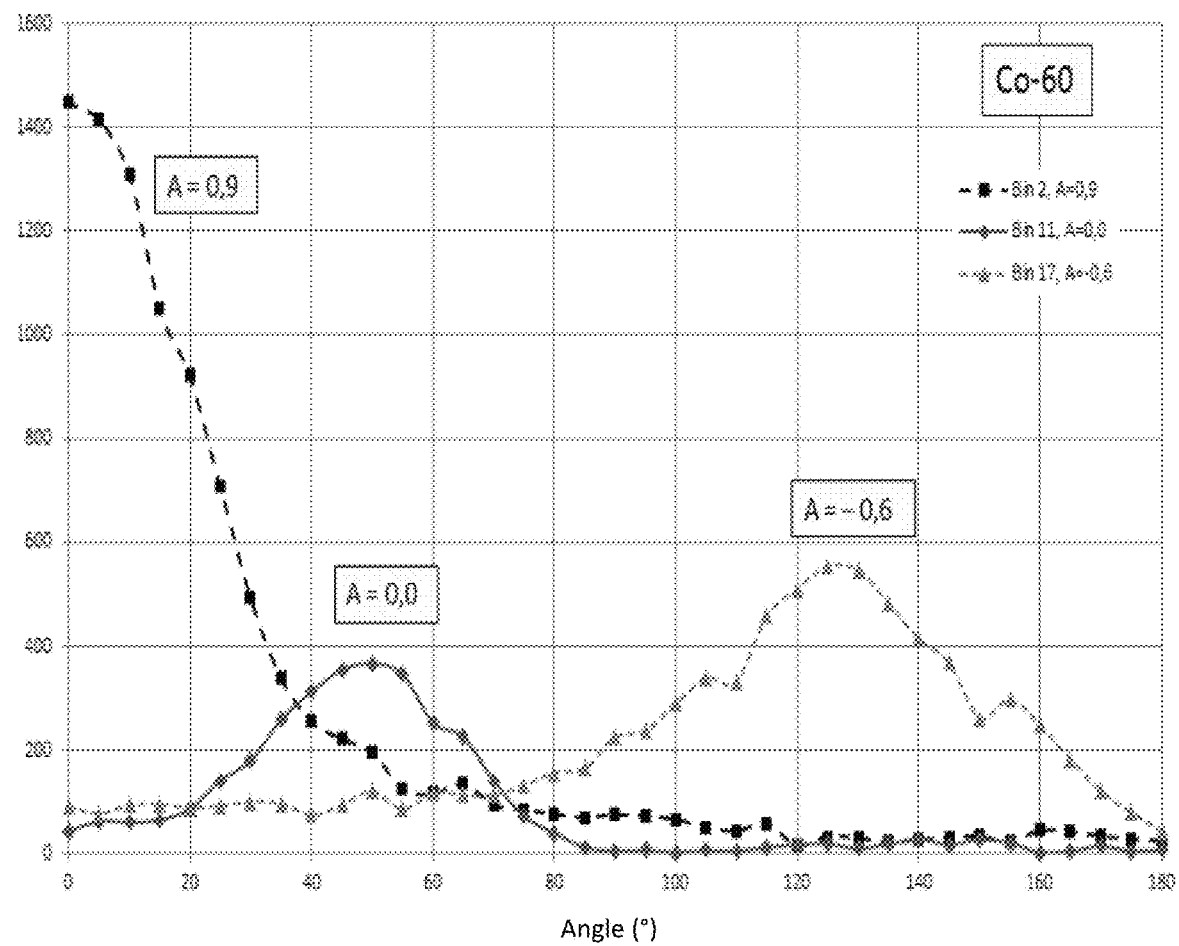
FIG. 10 is a diagram comprising measured functions of representation from a lookup table of the device module of FIG. 4a for $CeBr_3$—plastic detector pairs at selected asymmetry values A; according to a further embodiment of the invention.
Figure 11A:
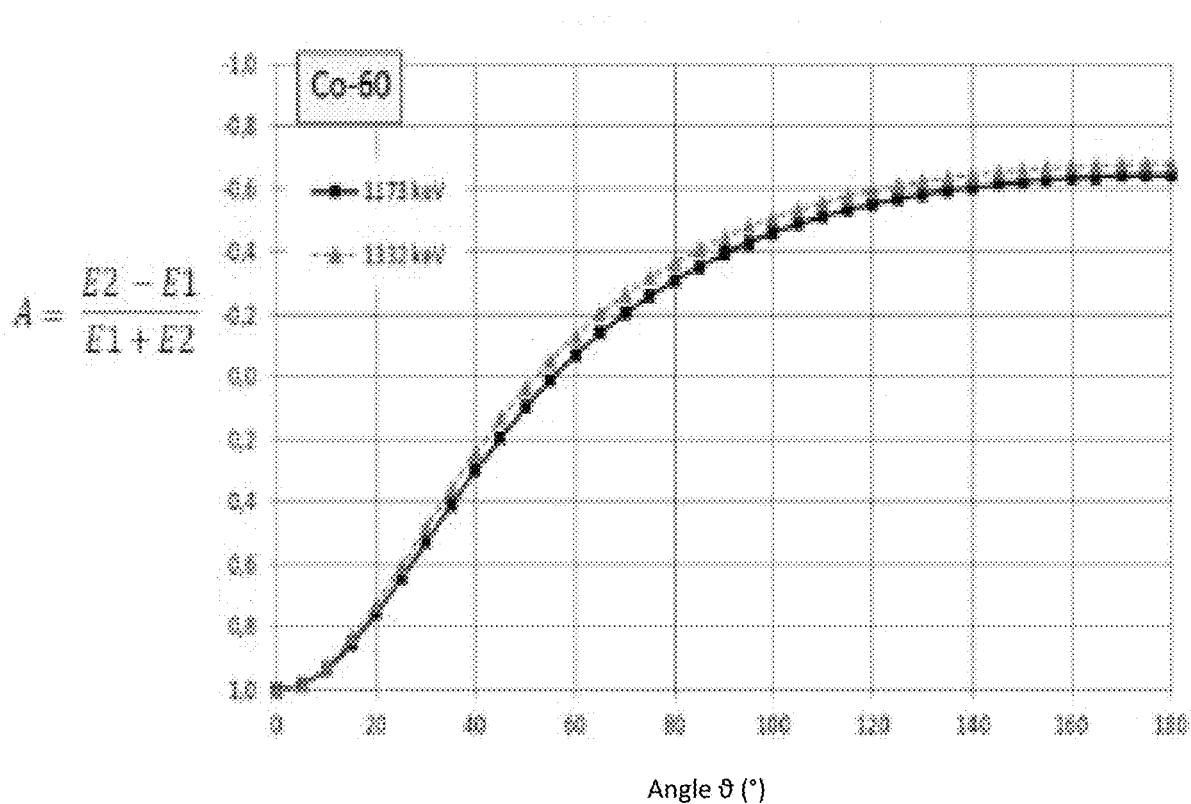
FIGS. 11a, 11b, 11c, and 11d illustrate four different diagrams of calculated asymmetry curves in the lookup tables of unidirectional and bidirectional detector pairs for the radio nuclides Co-60 and Cs-137, according to a further embodiment of the invention.
Figure 11B:
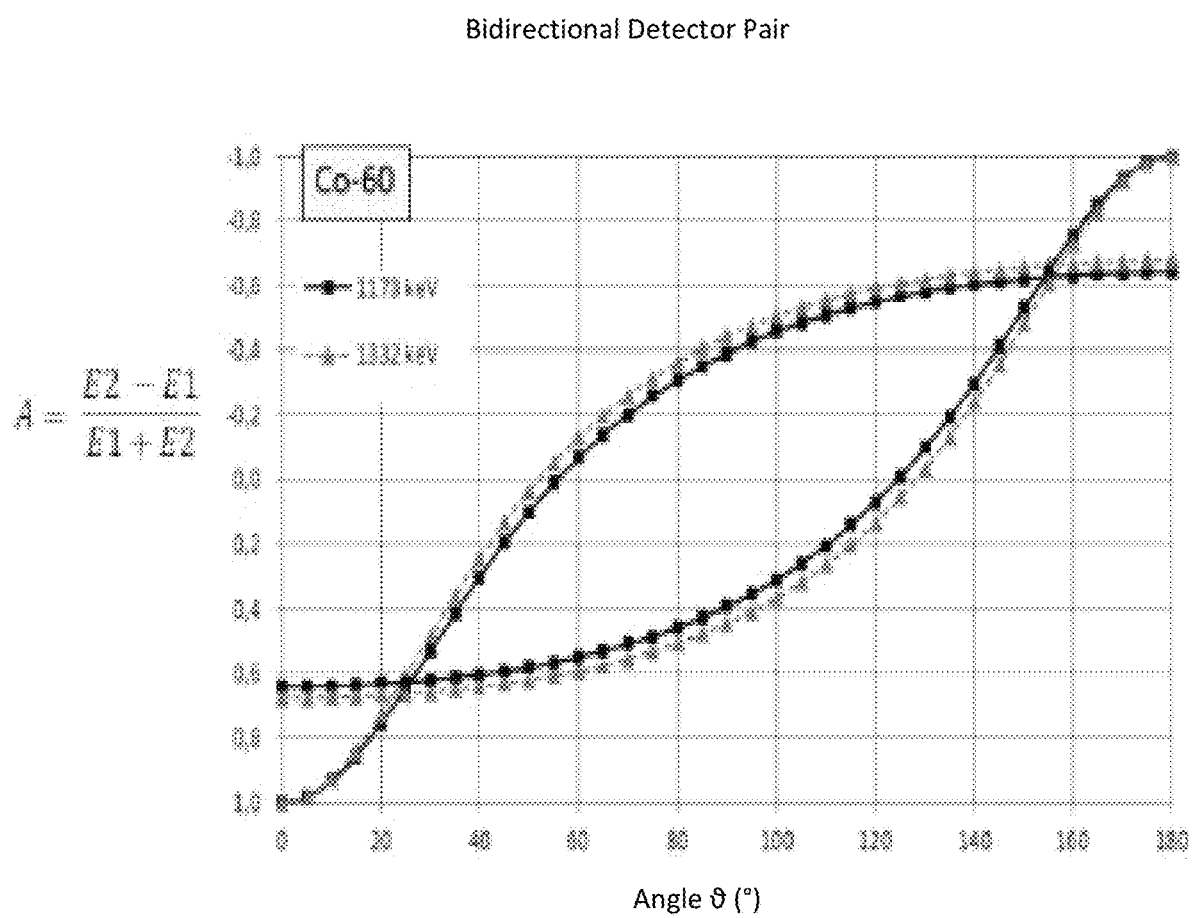
Figure 11C:
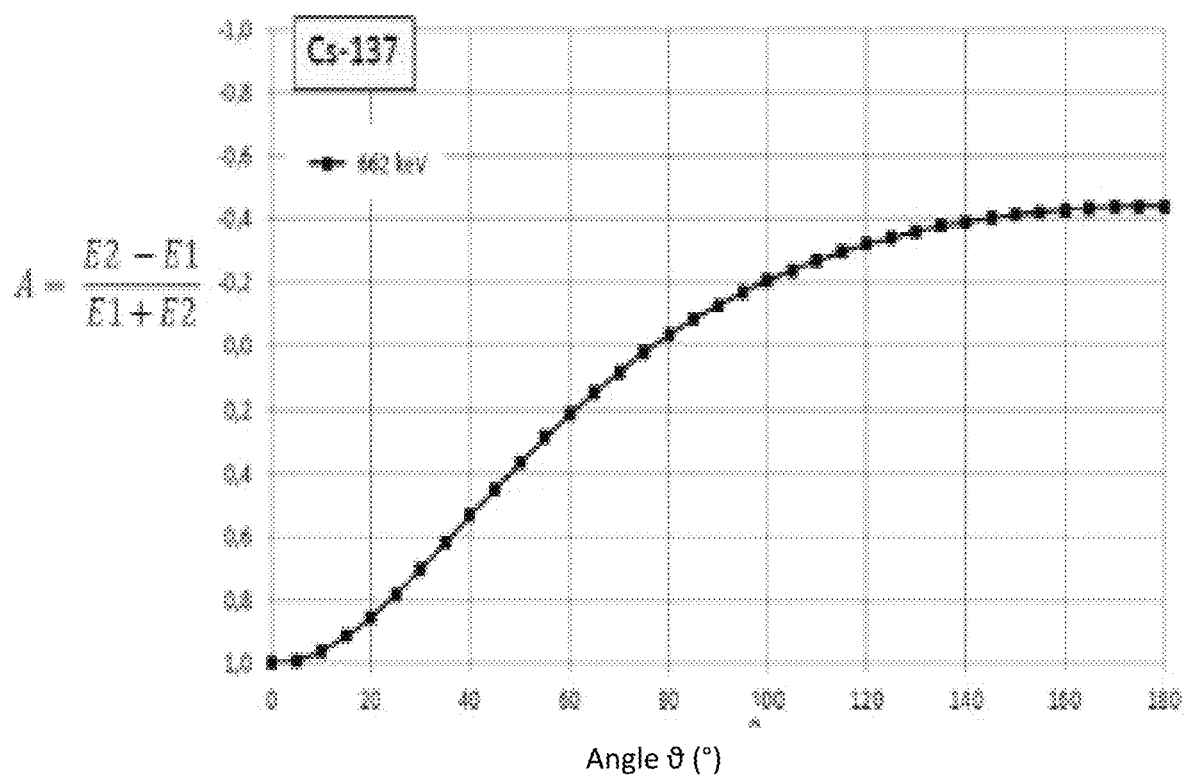
Figure 11D:
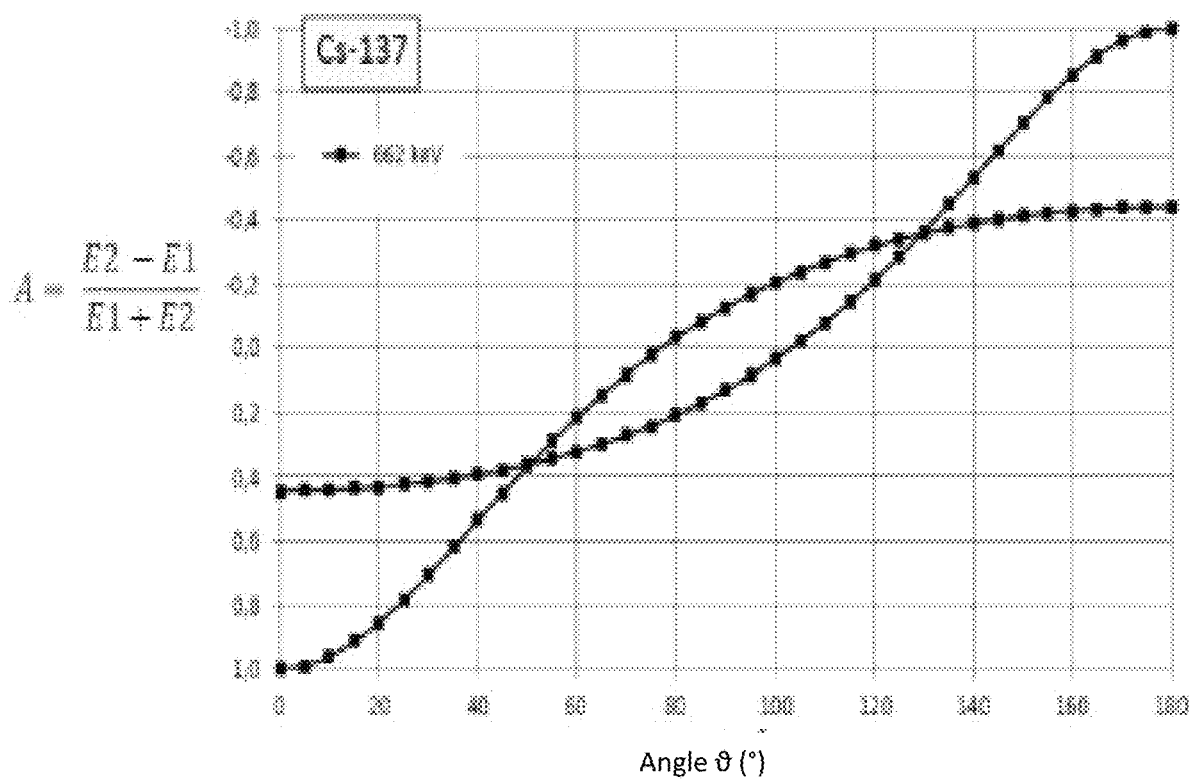

FIG. 10 shows various measured functions of representation from a lookup table for $CeBr_3$—plastic detector pairs at selected asymmetry values A. the functions of representation represent the frequencies according to which a radiation incident at an angle $\vartheta$ is registered in certain measurement value intervals A. A lookup table may be considered as a group of functions of representation. The example shows three of the functions recorded by means of a 10 µCi Co-60 source. Coincidence events of both Co-60 emission lines at 1173 keV and 1332 keV are stored together.

FIG. 11 shows asymmetry curves for lookup tables, which have been calculated for the radio nuclides Co-60 and Cs-137 according to an embodiment of the invention. The asymmetry curves show the areas in a lookup table with the highest frequencies. If there would be no measurement errors, all frequencies other than zero would be lying on the curves shown. Here, it is distinguished between lookup tables of unidirectional and bidirectional detector pairs. Lookup tables of unidirectional detector pairs (FIGS. 11a and 11c) are characterized by having only one prominent asymmetry curve. On the other hand, lookup tables of bidirectional detector pairs (FIG. 11b and FIG. 11d) have two prominent asymmetry curves. For Co-60, the asymmetry curves for both emission lines at 1173 keV and 1332 keV are illustrated; Cs-137 only has one emission line at 662 keV.

Figure 12:
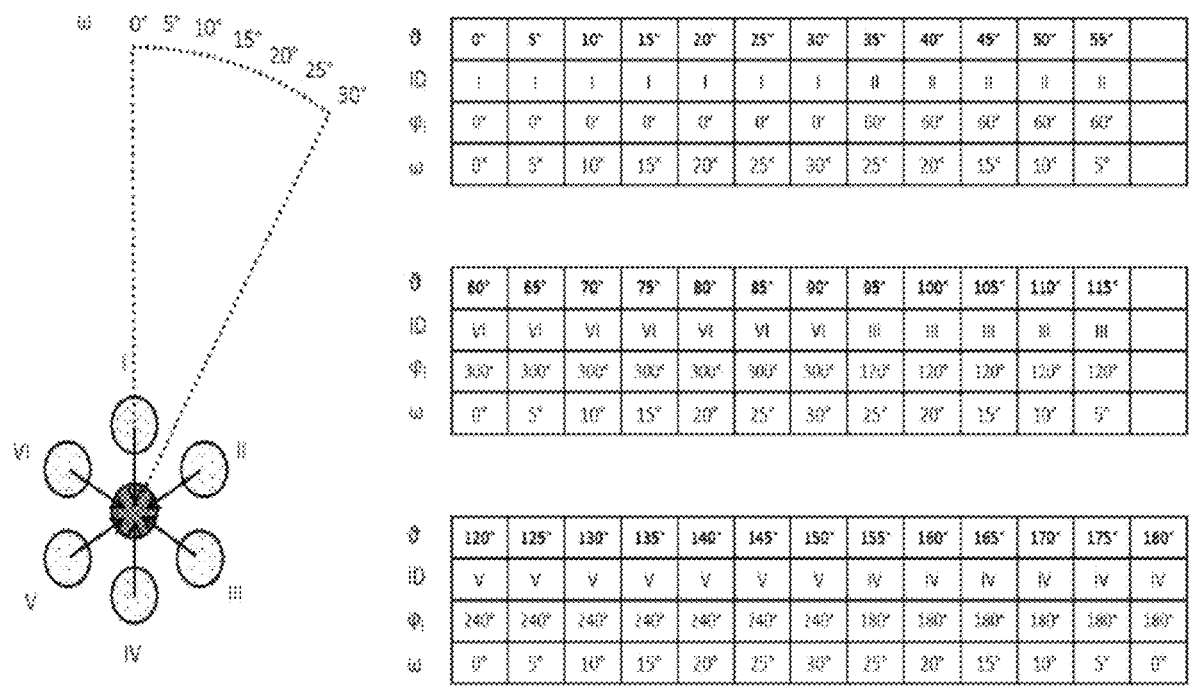
FIG. 12 shows a schematic illustration that is not to scale of a measurement plan with angular positions of a reference source for creating a lookup table for the device model of FIG. 4a according to a further embodiment of the invention.

FIG. 12 shows exemplarily the angular positions co of a measurement plan for creating the lookup table for the device model according to an embodiment of the invention shown in FIG. 4a. According to this plan, measurements are carried out at seven angular positions. The source, thereby, always has the same distance with respect to the center of the device. From these seven measurements, a lookup table may be created for the device model. In this example, the lookup table has a step size of 5°. For each angle $\vartheta$ in the value range from 0° to 180°, there is at least one detector pair, which has the correct angular distance with respect to the radiation source, and the data set of which can be copied into the respective location within the lookup tables. The measurement plan of FIG. 12 defines the assignments between the angular positions co of the reference source, the detector pairs, and the angular values $\vartheta$ of the lookup table.

Figure 13:
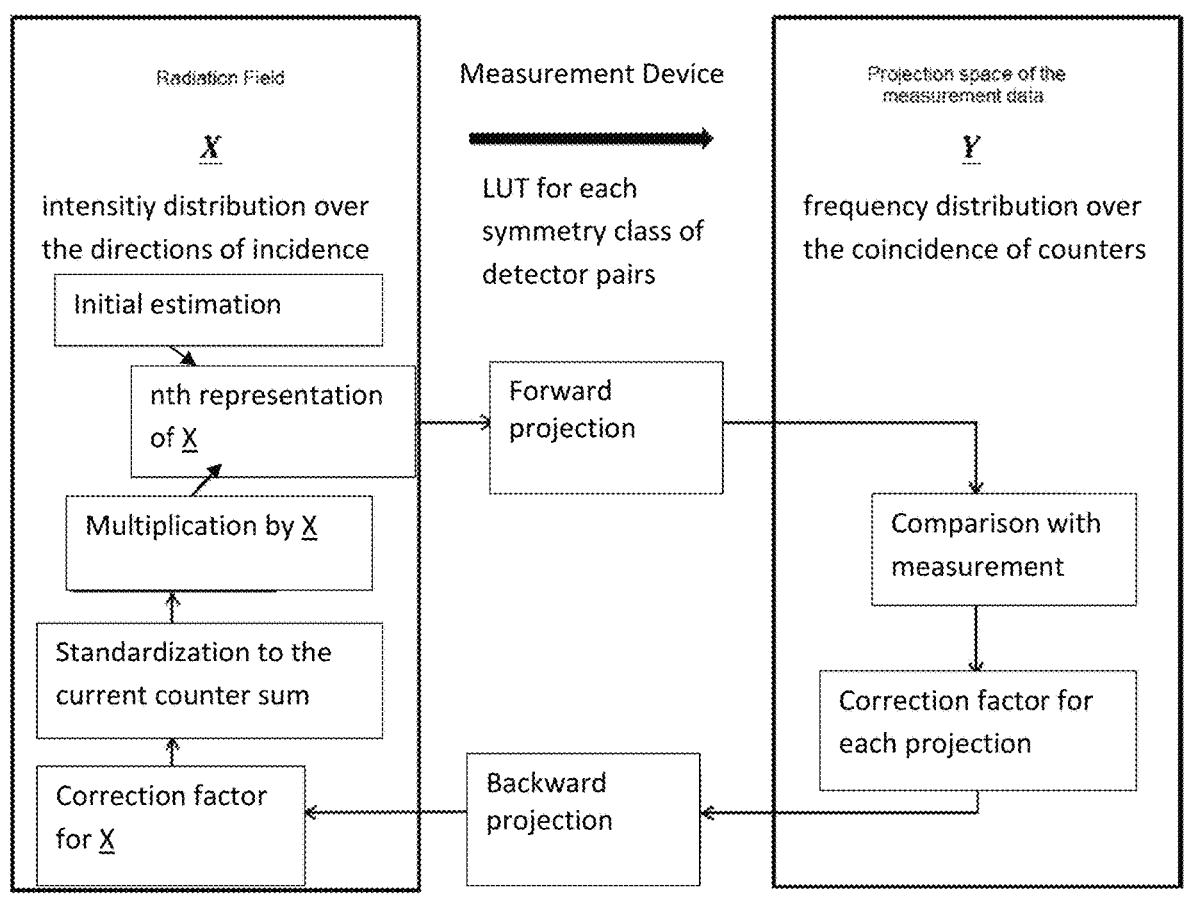
FIG. 13 shows a schematic illustration of a calculation scheme for an MLEM method for reconstruction of the direction distribution of a radiation field according to a further embodiment of the invention.

FIG. 13 shows a calculation scheme for an MLEM method for the reconstruction of the direction distribution of a radiation field according to an embodiment of the invention. With each iteration step n all calculation steps shown in FIG. 13 are carried out. With a progressing number n of iterations, the MLEM method leads to the direction distribution $\underline{X}$, which has the highest probability to have the observed frequency distribution $\underline{Y}$. The equations (13) and (16) comprise all calculation steps shown in FIG. 13 in compact form, including forward and backward projection.

Figure 14:
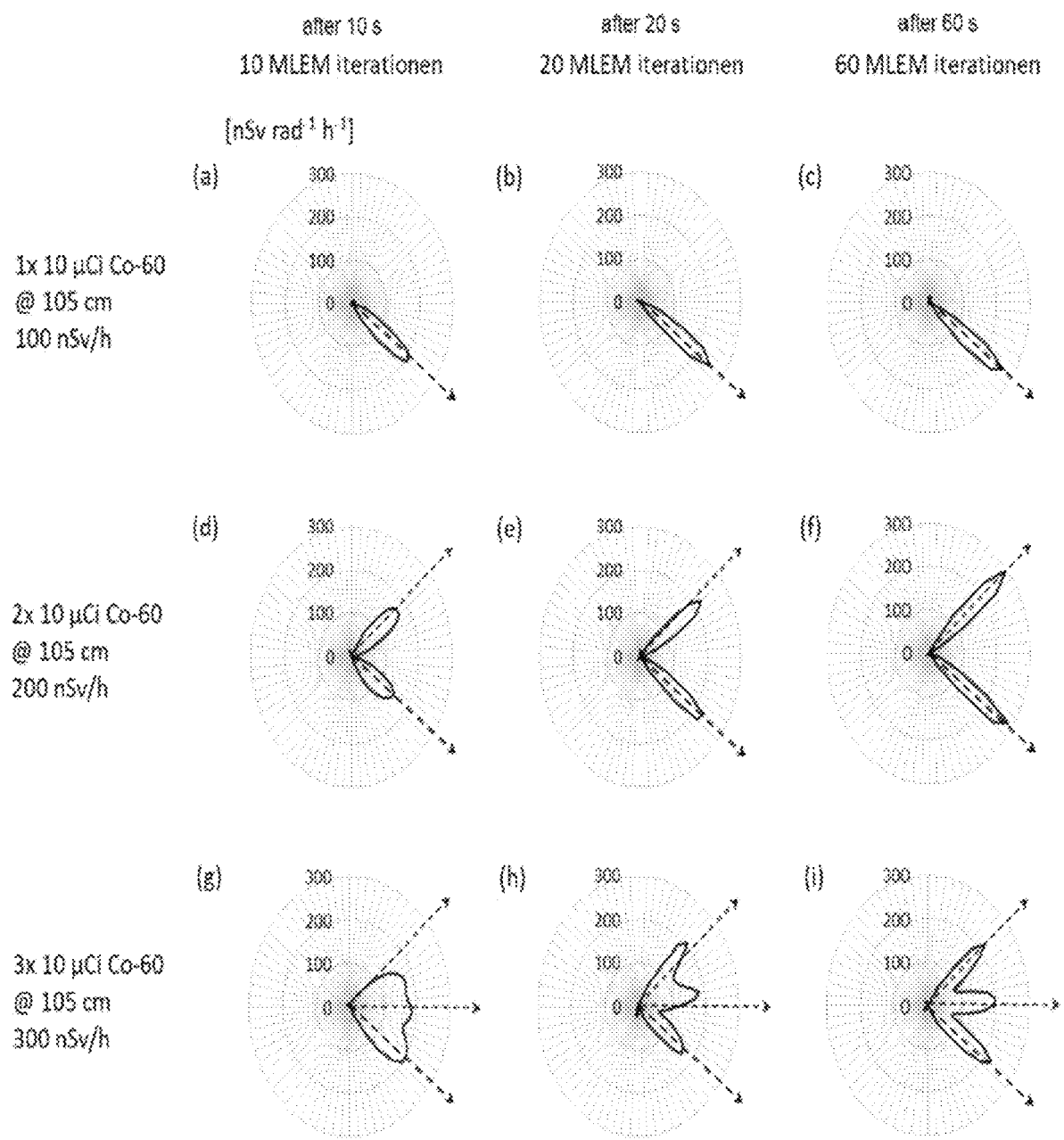
FIG. 14 shows nine diagrams of measurement direction distributions for radiation fields with one, two, and three point radiation sources. The illustrations are examples for 2-dimensional direction measurement by means of the device model of FIG. 4a, according to a further embodiment of the invention.

FIG. 14 shows various areas for 2-dimensional direction measurement by means of the device model of FIG. 4a. All measurements have been carried out respectively by 10 µCi Co-60 sources respectively in a distance of 105 cm. The radial measurement value scale is identical in all illustrations, and extends from 0 to 300 nSv rad' FIGS. 14a, 14b and 14c show measurement results for a Co-60 source at an angle of incidence of 125°. Subsequently, a second Co-60 source has been added at 50° and successively a third Co-60 source has been added at 90°. FIGS. 14d, 14e and 14f show the measurement direction distributions for the 2-sources-radiation field, FIGS. 14g, 14h and 14i for the 3-sources-radiation-field.

The method according to the invention as well as the device use unidirectional and bidirectional detection processes for the multidimensional direction measurement of gamma radiation. The direction measurement, which partially or completely uses bidirectional detection processes, has been described in the above mentioned embodiments in detail. The bidirectional direction measurement is based on the functional principle shown in FIG. 11, which will be explained briefly.

In contrast to unidirectional detection processes, which use a function of the connection between a measurement value (here, the asymmetry A) and the scattering angle $\vartheta$ for the direction measurement, bidirectional detection processes do not have such a calibration curve $A(\vartheta)$. The lookup tables of bidirectional detector pairs show two prominent structures along the asymmetry curves shown in FIGS. 11b and 11d. There are respectively two measurement values A1 and A2 belonging to a certain scattering angle $\vartheta$ which are observed at certain frequencies. Nevertheless, a certain scattering angle $\vartheta$ can be assigned uniquely to the value pair (A1, A2). Over the entire angular range from 0° to 180°, each value pair (A1, A2) exists exactly one time. It cannot be mistaken with any other value pair (A1, A2) at another angle D. Therefore, the scattering angle $\vartheta$ can also be measured by means of a bidirectional detector pair. Statistical reconstruction methods already comprise the functionality required for the direction measurement with bidirectional detector pairs. Methods as MLEM, therefore, are suitable for the processing of the measurement data from the device models according to the invention.

Here, measurements using the device model of FIG. 4a are presented, which are composed of six 3"×3" plastic-scintillation detectors and a 3"×3" cerbromide-scintillation detector. The six plastic detectors form a ring around the central cerbromide detector. The diameter of the detector ring is 25 cm.

Each one of the six plastic detectors may be combined with the central cerbromide detector into a unidirectional detector pair. In such a detector pair, the radiation is predominantly scattered in the plastic detector, and is absorbed in the cerbromide detector.

FIG. 14 shows measurement direction distributions for various arrangements of several point radiation sources. All measurements have been carried out by means of respectively 10 µCi Co-60 sources in a distance of respectively 105 cm. At first, a first Co-60 source has been placed at an angle of 125°. The dose rate generated by a 10 µCi Co-60 source in a distance of 105 cm is approximately 100 nSv $h^{-1}$. FIG. 14 a), b) and c) show the results of the direction measurements after respectively 10 s, 20 s and 60 s of measurement time. The number of the MLEM iterations has been dynamically coupled to the measurement time. With progressive measurement duration, the direction distribution of the point source becomes steeper and higher. The intensity averaged over all directions constantly amounts to 16 nSv $rad^{-1}$ $h^{-1}$. Integrated over the full angle of $2\pi$ rad a dose rate of $2\pi$ rad·16 nSv $rad^{-1}$ $h^{-1}$=100 nSv $h^{-1}$ is obtained. Subsequently, a second Co-60 source has been added at 50°. The designs are shown in FIG. 14 d), e) and f). The presence of two sources can already be seen at a measurement time of 10 s. The intensity averaged over all directions now amounts to 32 nSv $rad^{-1}$ $h^{-1}$. Finally, a third Co-60 source has been added to the arrangement at 90°. The results in FIG. 14 g), h) and i show that from a measurement time of 20 s on, also three point sources can be resolved separately.

A methodology has been developed, by means of which the quality of the direction measurement can be formulated as a time specification, from which on a reliable direction measurement is available. The aim of this procedure was to quantitatively evaluate the quality of the direction measurement of a point source depending on the type of the nuclide, the dose rate, and the angular position. As sources, a Co-60, a Cs-137 and a Co-57 of an activity of respectively 10 µCi have been available, respectively.

Two quality classes have been defined: ±5° and ±10° angular accuracy. At each point of time t during a measurement, the MLEM method provides an estimated value for the direction of the radiation source. The measurements respectively have been run for a certain measurement time and have been repeated 20 times. Now, at each point of time t it can be determined, how many of the measurements fall into the ±5° or ±10° quality class. A confidence level of 90% has been selected. $t_{90}$ is defined as that time, from which on at least 18 of the 20 measurements are correct, that means are lying within a ±5° or ±10° interval around the true value. In 90% of all measurements, the specified accuracy has been reached or exceeded after the minimum measurement time.

The device model of FIG. 4a has a characteristic asymmetry. At first, it has been examined, which influence the device specific detector arrangement has on the minimum measurement times, which are measured at different angles of incidence. The sensitivity of the direction measurement depends on the position of the source with respect to the device. If the source is located towards one of the six ring detectors, longer measurement times are required than in a case in which the source is lying in the center between two ring detectors. In this study, all sources had a constant distance of 1 m with respect to the center of the device. The minimum measurement time $t_{90}$ for ±10° accuracy of the 10 µCi Co-60 source was 2.7 s towards the ring detectors, and has shortened to 0.5 s in the middle between two ring detectors. A similar behavior has been observed for Cs-137. Here, the minimum measurement time $t_{90}$ for ±10° accuracy was 5.8 s towards the ring detectors, and has shortened to 0.7 s in the middle between two ring detectors.

Next, it has been examined, how the $t_{90}$ minimum measurement time depend on the dose rate. These measurements have been carried out respectively in the direction of the ring detectors. They represent the lower limit of the performance of the device. The distance of the sources has been varied from 1 to 5 meters. The dose rate has been expressed as the local dose rate $\dot{H}^*(10)$ of the source at the measurement point. Thereby, it has been determined that above 0.05 µSv/h, the product of local dose rate $\dot{H}^*(10)$ and $t_{90}$ minimum measurement time is constant.

With this condition, the $t_{90}$ minimum measurement times may be parameterized by the simple analytic expression $$t_{90} = T(Nuklid, \sigma) \cdot \left(\frac{\dot{H}^*(10)}{\mu Sv/h}\right)^{-1} \tag{44}$$

The parameters T(Nuklid, σ) are device specific parameters, which are defined depending on the type of nuclide and the quality class σ. For the device model with six 3"×3" plastic detectors and one 3"×3" cerbromide detector, the parameters have been determined as follows: T($^{60}$Co, ±10°)=0.32 s, T($^{60}$Co, ±5°)=0.48 s, T($^{137}$Cs, ±10°)=0.16 s and T($^{137}$Cs, ±5°)=0.24 s.

It also has been examined, how the direction measurement behaves at very low local dose rates. Also below 0.05 µSv/h, direction measurements of high-quality are possible, the required measurement times are getting longer then, and possibly lie above the value calculated by means of $$t_{90} = T(Nuklid, \sigma) \cdot \left(\frac{\dot{H}^*(10)}{\mu Sv/h}\right)^{-1}.$$

By means of the available device model, it was possible without any difficulties to also measure the direction of the source reliably with an accuracy of ±5° with only few nSv/h. Then, the measurement times are lying in the range of some minutes. For example, the direction measurement for a Co-60 source with 3 nSv/h dose rate after 140 s has an accuracy of ±10° and after 220 s an accuracy of ±5°. A Cs-137 source with 4 nSv/h dose rate at the measurement location could be detected after 55 s with ±10° and after 90 s with ±5°. The direction measurement of a Co-57 source with 5 nSv/h dose rate, after 22 s had an accuracy of ±10° and after 35 s had an accuracy of ±5°.

If almost static measurement conditions are prevailing, the direction measurement may be carried out in a clocked manner. Then, it is possible, for example, to track the movement of the radiation sources. The dose rate $\dot{H}^*(10)$, in turn, is a suitable value for controlling the clock frequency. If, for example, the movement of a point source is to be tracked, the clock frequency may be set to the time $t_{90}$.

For an experiment with almost static measurement conditions, the device model of FIG. 4a has been mounted on a rotary plate. The clock frequency of the measurement program has been set to the time $t_{90}$. At a rotation speed of 0.2 rounds per minute, the current position of a 10 µCi Co-60 source could be tracked in a distance of 1 m.

The present invention has been described by means of some specific embodiments of the devices and methods. Persons skilled in the art in the field of radiation detection, of course, are able to modify these embodiments without departing from the principles and the spirit of the invention, the scope of protection of which is defined in the claims and its equivalents.

The invention claimed is:

1. A method for the multidimensional direction measurement of gamma radiation in the far field via a group of several energy discriminating detectors synchronized with each other for detecting radiation, wherein the method uses unidirectional and bidirectional Compton scattering processes and lookup tables LUT$^{SK}$, a defined functional value f(E1, E2), a list of defined detector pairs with an identification number i for defined detector pairs, and one or more frequency distributions $\underline{Y}$ for acquiring the measurement values, and the method comprises:
   a) setting up the detector system for a measurement, wherein the following sequence of steps is carried out:
   creating a list with defined detector pairs, wherein the defined detector pairs comprise all pairs, which may be formed in combination from the quantity of the detectors, and wherein each pair comprises at least one detector made from a material having an atomic number of $Z_{eff}$>30, and identifying the latter with an ID number i;
   interconnecting all detectors in a coincidence circuit such that coincidence events are acquired in all defined detector pairs i=1, . . . , I;
   identifying both detectors of each defined detector pair i with the numbers 1 and 2, respectively, wherein the detector having the lower atomic number receives the number 1, and that one having the higher atomic number receives the number 2, wherein in case both detectors consist of the same material, the identification as 1 and 2, respectively, is made arbitrarily;

defining a function f(E1, E2), which is calculated from two energy values E1 and E2, wherein such functions f(E1, E2) are allowable, which are traceable back to a function f(E1) when substituting E2 by C-E1, which function over the entire interval [0,C] is clearly defined, constant, and monotonous; wherein C is a constant, which represents the radiation energy C=E1+E2;

b) acquiring measurement values of coincidence events, if interactions take place simultaneously in respectively two detectors of all defined detector pairs i, wherein the measurement values originate from a radiation distribution in the far field, and the measurement values are the interaction energies E1 and E2 of the radiation measured in the detectors;

c) associating coincidence events with an identification number i;

d) calculating the functional value f(E1, E2) from two energy values E1, E2 per coincidence event by means of the function f(E1, E2) defined in step a);

e) acquiring the coincidence events corresponding to their identification number i and their functional values f(E1, E2) in one or more frequency distributions $\underline{Y}$, wherein a separate frequency distribution $\underline{Y}$ is available for each radio nuclide, f) calculating one or more direction distributions $\underline{X}$ from the frequency distributions $\underline{Y}$ by means of a statistic image reconstruction method of emission tomography using lookup tables $LUT^{SK}$, wherein a separate direction distribution $\underline{X}$ is available for each radio nuclide.

2. The method of claim 1 wherein: the radiation sources emit a discrete and/or continuous distribution of radiation; and/or that the radiation sources emit gamma, electron, positron, proton, ion, and/or neutron radiation; and/or that the radiation originates from the radioactive decay of one or more radio nuclides; and/or that the radiation is the prompt gamma radiation, which is generated during the absorption of proton or ion radiation in target materials; and/or that the radiation is of low intensity, as, for example, in astronomy.

3. The method of claim 2, wherein the method in step a) also comprises at least one of:

calibrating the signals of all detectors as absorbed radiation energy E;

determining a suitable coordinate system;

acquiring the directions of the defined detector pairs, wherein in the 2-dimensional direction measurement, the direction of the detector pair i is acquired with the azimuth angle $\varphi_i$, and wherein in the 3-dimensional direction measurement, the direction of detector pair i is acquired with the azimuth angle $\varphi_i$ and the height angle $\beta_i$;

dividing the measurement range for the functional value f(E1,E2) into a number J of equidistant measurement value channels j=1, . . . , J;

creating one or more 2-dimensional arrays with I·J fields as data structures for storing the frequency distributions $\underline{Y}$, in which coincidence events are registered according to their ID number i and are registered according to their measurement value channel j;

wherein a separate 2-dimensional array $\underline{Y}$ is created for each radio nuclide;

dividing the detector pairs i into symmetry classes SK, wherein those detector pairs i, which are mapped to other detector pairs with similar construction upon rotation or translation are aggregated to respectively one symmetry class SK(i);

creating one or more lookup tables $LUT^{SK}$ for each symmetry class SK and for each radio nuclide, wherein these cover an angular range $\vartheta$ from 0° to 180° and are divided into equidistant angular steps;

creating the lookup tables $LUT^{SK}$ by measurements with the detector system or by Monte Carlo simulations or by means of a theoretical model;

transferring all lookup tables $LUT^{SK}$ for all symmetry classes and all radio nuclides to an algorithm of image reconstruction, which processes the measurement data and which calculates the direction distributions $\underline{X}$.

4. The method of claim 3, wherein the lookup tables $LUT^{SK}$ are created by measurements with the detector system by a creation process comprising:

creating a prescription for generating and validating the lookup tables $LUT^{SK}$ from reference measurements, which selects the reference sources, considers the nuclide type, as well as defines the measurement conditions, under which the measurements are to be carried out;

performing reference measurements for all steps defined previously in the prescription;

creating and validating the lookup tables $LUT^{SK}$ according to the prescription defined previously for analyzing the measurement data of the reference measurements;

detecting the natural radiation background $b^{SK(i)}$ for all symmetry classes SK;

excluding the natural radiation background $b^{SK}$ from the lookup tables $LUT^{SK}$.

5. The method of claim 1, wherein the functional value f(E1, E2) used in steps a) and d) is energy asymmetry f(E1, E2)=(E2−E1)/(E1+E2).

6. The method of claim 1, wherein:

the selection condition for the energy sum E1+E2 of the energies detected in both detectors of a pair is applied;

and/or that for each radio nuclide, a separate frequency distribution $\underline{Y}$ is created;

and/or that for each radio nuclide, a separate direction distribution $\underline{X}$ is calculated.

7. The method of claim 1, wherein:

several selection conditions are applied for the energy sum E1+E2 for radio nuclides with several gamma energies;

and/or that for such radio nuclides with several gamma energies, one or more frequency distributions $\underline{Y}$ are created.

8. The method according to claim 1, characterized in that in step f), the statistic image reconstruction method partially or completely is the Maximum Likelihood Expectation Maximization (MLEM) method, the Ordered Subset Expectation Maximization (OSEM) method, the List Mode-Maximum Likelihood Expectation Maximization (LM-MLEM) method and/or the List Mode-Ordered Subset Expectation Maximization (LM-OSEM) method.

9. The method of claim 1, wherein, for each detected radio nuclide, a 2-dimensional direction distribution $X_k=X(\omega_k)$ is calculated according to $$X_k^{[n+1]} = X_k^{[n]} \frac{K}{\sum_{i,j} Y_{ij}} \sum_{i,j} \frac{LUT_j^{SK(i)}[\vartheta(\omega_k, \varphi_i)]Y_{ij}}{\sum_{k'=1}^{K} LUT_j^{SK(i)}[\vartheta(\omega_{k'}, \varphi_i)]X_{k'}^{[n]}}$$

from the initial distribution $$\forall k=1,\ldots,K\ X_k^{[0]}=1$$

using the lookup tables $LUT^{SK}$ and an angular distance function according to $$\vartheta(\omega_k,\varphi_i)=\arccos(\cos(\omega_k-\varphi_i))$$

wherein K is a number of pixels for the azimuth angle $\omega_k$ defined by the user.

10. The method of claim 1, wherein, for each detected radio nuclide, a 3-dimensional direction distribution $X_{kl}=X(\omega_k, h_l)$ is calculated according to $$X_{kl}^{[n+1]} = X_{kl}^{[n]}\frac{KL}{\sum_{i,j}Y_{ij}}\sum_{i,j}\frac{LUT_j^{SK(i)}[\vartheta(\omega_k,h_l,\varphi_i,\beta_i)]Y_{ij}}{\sum_{k'=1}^{K}\sum_{l'=1}^{L}LUT_j^{SK(i)}[\vartheta(\omega_{k'},h_{l'},\varphi_i,\beta_i)]X_{k'l'}^{[n]}}$$

from the initial distribution $$\forall k=1,\ldots,K,l=1,\ldots,L\ X_{kl}^{[0]}=1$$

using the lookup tables $LUT^{SK}$ and an angular distance function according to $$\vartheta(\omega_k,h_l,\varphi_i,\beta_i)=\arccos(\cos\beta_i\cos h_l\cos(\omega_k-\varphi_i)+\sin\beta_i\sin h_l)$$

wherein K and L are numbers of pixels defined by the user for the azimuth angle $\omega_k$ and the height angle $h_l$.

11. A device for carrying out a method for multidimensional direction measurement of gamma radiation in a far field, comprising:
a group of several synchronized detectors for detection of radiation, wherein at least one detector material has an atomic number $Z_{eff}>30$ and all detectors measure the energies E, which occur in interactions of the radiation with the detector materials;
a system electronics, which registers coincidence events, if interactions take place simultaneously in respectively two detectors from a list of defined detector pairs i, wherein the list of defined detector pairs comprises all pairs, which can be formed in combination from the quantity of all detectors, and wherein the defined detector pairs comprise at least one detector made from a material having an atomic number of $Z_{eff}>30$;
a data acquisition system, which determines a ranking for both detectors involved in a coincidence event, which defines a first and a second detector, and which sorts the energies (E1, E2) measured in the coincidence events corresponding to their identification 1, 2 and stores them in a chronological list with the attributes {i, E1, E2} and the detection time t; wherein in each detector pair i the detector having the lower atomic number receives the number 1, and that one having the higher atomic number receives the number 2, wherein if both detectors of a pair should have the same atomic number, the identification of 1 and 2, respectively, is made arbitrarily; and
an analysis unit, which creates one or more frequency distributions $\underline{Y}$ from the data stored in the data acquisition system, wherein a function f(E1, E2) is applied, which is dependent on two energy values (E1, E2), and wherein this function f(E1, E2) is traceable back to a function f(E1) when substituting E2 by C-E1, which function over the entire interval [0,C] is clearly defined, constant, and monotonous, wherein C is a constant, which represents the radiation energy C=E1+E2, and an analysis unit, which reconstructs one or more direction distributions $\underline{X}$ of the radiation field.

12. The device according to claim 11, wherein the device is configured partially or completely as a Compton camera, a Compton telescope, a single plane Compton camera, a neutron camera, and/or a dual gamma/neutron camera;
and/or wherein the entirety of all detectors is arranged in a ring, and/or wherein one or more central detectors may be present in the interior of the ring;
and/or wherein the ring preferably comprises four of five, and particularly preferred six plastic-scintillation detectors, and/or one or more scintillation detectors made from NaI, CsI, $CeBr_3$ and/or $LaBr_3$ are provided in the interior of the ring;
and/or the scintillation detectors preferably are formed with a dimension of 1"×1", 1,5"×1.5", 2"×2" and/or 3"×3".

13. The device of claim 12, wherein a scintillation detector is used as the detector, and/or the scintillator is formed as monolithic block or as pixelated scintillator module, and/or which is made from pure or doped materials from the group of PVT, anthracene, stilbene, p-terphenyl, $CaF_2$, $BaF_2$, NaI, $CeBr_3$, $LaBr_3$, $LaCl_3$, $La(Br_xCl_{1-x})_3$, CsI, $SrI_2$, CLYC, CLBC, CLCB, CLLB, BGO, LSO, LYSO, GAGG, YAP and/or YAG;
and/or that a semiconductor detector is used as detector, and/or that the semiconductor is formed as segmented or non-segmented semiconductor, and/or which has a planar or coaxial geometry, and/or which is made from materials of the group of Ge, GaAs, CdTe and/or CdZnTe.

14. The device of claim 13, wherein at least two detectors are used;
and/or that all detectors used are substantially similar in construction, and that at least two of the detectors used are different from each other.

15. The device of claim 11, wherein a detector and system electronics is used, which uses analog and/or digital electronic components;
and/or that the analog electronic components comprise a combination of various modules, which comprise a high-voltage supply, a preamplifier, an amplifier, a pulse shaper, the charge integrator, a pulse height analyzer, a multichannel analyzer (MCA) and/or a coincidence circuit;
and/or that the digital electronic components comprise a combination of different hardware and software components, which comprise a high-voltage supply, an A/D converter per detector, a Field Programmable Gate Array (FPGA), a storage medium, a digital signal processor, and/or an analysis software.

* * * * *